(12) United States Patent
Remes et al.

(10) Patent No.: US 11,933,770 B2
(45) Date of Patent: *Mar. 19, 2024

(54) METHODS AND APPARATUS FOR TARGETED MASS SPECTRAL PROTEOMIC ANALYSES

(71) Applicant: Thermo Finnigan LLC, San Jose, CA (US)

(72) Inventors: Philip M. Remes, Livermore, CA (US); David A. Sarracino, Belmont, MA (US); Sebastien F. Gallien, Genlis (FR)

(73) Assignee: Thermo Finnigan LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,003

(22) Filed: Nov. 2, 2022

(65) Prior Publication Data
US 2023/0408463 A1    Dec. 21, 2023

Related U.S. Application Data

(62) Division of application No. 16/856,987, filed on Apr. 23, 2020, now Pat. No. 11,493,487.

(51) Int. Cl.
G01N 30/00    (2006.01)
G01N 30/72    (2006.01)
(Continued)

(52) U.S. Cl.
CPC ..... *G01N 30/7233* (2013.01); *G01N 30/8637* (2013.01); *G01N 30/8641* (2013.01);
(Continued)

(58) Field of Classification Search
CPC ........... G01N 30/7233; G01N 30/8637; G01N 30/8641; G01N 30/8675; G01N 33/6848;
(Continued)

(56) References Cited

U.S. PATENT DOCUMENTS 8,383,417 B2  2/2013  Lopez et al.
9,911,585 B1  3/2018  Zabrouskov
(Continued)

OTHER PUBLICATIONS

Bantscheff M et al., "Quantitative Mass Spectrometry in Proteomics: Critical Review Update from 2007 to the Present," Analytical and Bioanalytical Chemistry, Springer, Berlin, DE, vol. 404, No. 4, Jul. 8, 2012 (Jul. 8, 2012), pp. 939-965, XP035098917, ISSN: 1618-2650, DOI:10.1007/S00216-012-6203-4.
(Continued)

*Primary Examiner* — Michael Maskell
(74) *Attorney, Agent, or Firm* — Thomas F. Cooney

(57) ABSTRACT

A Liquid Chromatography Mass Spectrometry system comprises: a chromatograph; a mass spectrometer configured to ionize separated fractions of a sample received from the chromatograph; and a programmable processor operable to repeatedly execute the steps of: (i) causing the mass spectrometer to perform a data-independent analysis of the precursor ion species using a mass analyzer of the mass spectrometer; (ii) calculating one or more degree-of-matching scores that relate to detection of an internal standard; and (iii) if each of the degree-of-matching scores meets a respective degree-of-matching condition, performing a quantitative tandem mass spectrometric analyses of both the internal standard and the analyte; the programmable processor further operable to calculate a quantity of the analyte in the sample by comparison between intensities of one or more mass spectral signals generated by the quantitative tandem mass spectrometric analyses of the analyte and the internal standard.

21 Claims, 17 Drawing Sheets

(51) Int. Cl.
  *G01N 30/86* (2006.01)
  *G01N 33/68* (2006.01)
  *H01J 49/00* (2006.01)
  *H01J 49/42* (2006.01)

(52) U.S. Cl.
  CPC ..... *G01N 30/8675* (2013.01); *G01N 33/6848* (2013.01); *H01J 49/004* (2013.01); *H01J 49/4265* (2013.01); *G01N 2458/15* (2013.01); *G01N 2570/00* (2013.01)

(58) Field of Classification Search
  CPC ........... G01N 2458/15; G01N 2570/00; G01N 2030/8831; G01N 30/8679; H01J 49/004; H01J 49/4265
  USPC ................................................. 250/281, 282
  See application file for complete search history.

(56) References Cited

U.S. PATENT DOCUMENTS

| 11,493,487 | B2* | 11/2022 | Remes ............... G01N 30/7233 |
| 2006/0289737 | A1 | 12/2006 | Bassmann et al. |
| 2009/0189073 | A1 | 7/2009 | Yamaguchi |
| 2014/0138537 | A1 | 5/2014 | Grothe, Jr. et al. |
| 2017/0069475 | A1 | 3/2017 | Brown |

OTHER PUBLICATIONS

Blackburn K et al., "Challenges and Strategies for Targeted Phosphorylation Site Identification and Quantification Using Mass Spectrometry Analysis," Briefings in Functional Genomics and Proteomics, London, GB, vol. 8, No. 2, Mar. 1, 2009 (Mar. 1, 2009), pp. 90-103, XP009134756, ISSN: 1473-9550, DOI: 10.1093/BFGP/ELN051.

Egertson et al., "Multiplexed MS/MS for improved data independent acquisition", Nature Methods, 2013, vol. 10 (8), pp. 744-748.

Gallien et al., Large Scale Targeted Proteomics Using Internal Standard Triggered-Parallel Reaction Monitoring (IS-PRM), Tecnological Innovation and Resources by the American Society for Biochemistry and Molecular Biology, Inc., 2015, pp. 1630-1644.

Gerber S.A., et al., "Absolute Quantification of Proteins and Phosphoproteins from Cell Lysates by Tandem MS," Proceedings of the National Academy of Sciences, National Academy of Sciences, US, Jun. 10, 2003, vol. 100, No. 12, pp. 6940-6945, XP002360986, ISSN: 0027-8424. DOI:10.1073/PNAS.0832254100.

Gillet, et al., "Targeted Data Extraction of the MS/MS Spectra Generated by Data-independent Acquisition: A New Concept for Consistent and Accurate Proteome Analysis", Molecular & Cellular Proteomics 11.6, 2012, pp. 1-17.

Ozdian et al., "Cancer Proteomics in Clinical and Experimental Oncology," Thesis, Sep. 1, 2016 (Sep. 1, 2016), pp. 1-182, XP055505785, Retrieved from the Internet: URL: https://theses.cz/id/cppbbd/dizertace0_dian.pdf [retrieved on Sep. 1, 2021].

Peisl et al., "Dark matter in host-microbiome metabolomics: Tackling the unknowns—A review", Analytica Chimica Acta 1037 (2018), pp. 13-27.

Rauniyar N: "Parallel Reaction Monitoring: A Targeted Experiment Performed Using High Resolution and High Mass Accuracy Mass Spectrometry," International Journal of Molecular Sciences, vol. 16, No. 12, Dec. 2, 2015 (Dec. 2, 2015), pp. 28566-28581, XP055389549, DOI: 10.3390/ijms161226120.

Venable et al., "Automated approach for quantitative analysis ofcomplex peptide mixtures from tandem mass spectra", Nature Methods, 2004, vol. 1 (1), pp. 1-7.

Wan et al., "Comparing Similar Spectra: From Similarity Index to Spectral Contrast Angle", J Am Soc Mass Spectrom 2002, 13, pp. 85-88.

* cited by examiner

METHODS AND APPARATUS FOR TARGETED MASS SPECTRAL PROTEOMIC ANALYSES

CROSS REFERENCE TO RELATED APPLICATION

This application is a Divisional of co-pending and commonly-assigned U.S. patent application Ser. No. 16/856,987, titled "Methods and Apparatus for Targeted Mass Spectral Proteomic Studies", now U.S. Pat. No. 11,493,487, which was filed on Apr. 23, 2020, the disclosure of which is hereby incorporated herein by reference in its entirety.

TECHNICAL FIELD

The present disclosure relates to mass spectrometers and mass spectrometry. In particular, the present disclosure relates to targeted quantitative mass spectral analysis of proteins.

BACKGROUND

Mass spectrometry is a well-established technology for analyzing for the presence and concentration (or amount) of a wide variety of chemical constituents with high sensitivity. One area of research and study for which mass spectrometry has proven to be particularly useful is the field of proteomics. Proteomics studies frequently take the form of simultaneous quantitative analysis of a plurality of target proteins through surrogate peptides generated by enzymatic digestion in biological samples. Such studies typically employ the technique of tandem mass spectrometry, often referred to as MS/MS or MS-2 mass spectrometry, in which particular peptide precursor ions are selected, isolated and fragmented (e.g., in a collision cell), and the resulting fragment (product) ions are mass analyzed in a mass analyzer. The mass analysis generates a record of the intensities of the various fragment ion species as a function of their mass-to-charge ratio (m/z) values. Calibration of the intensity scale, perhaps by comparison to internal standard compounds (synthetic isotopically labeled forms of surrogate peptides) introduced into the sample in known amounts, provides a measure of the concentration, within the sample, of the target protein from which the peptide ion species were generated. The MS-2 method can be extended by further fragmentation of selected and isolated fragment ion species, and so on, with possible mass analysis of the resulting fragments for each generation. Such extensions of the tandem mass spectrometry technique are typically referred to an MS-n spectrometry, with n indicating the number of steps of mass analysis and the number of generations of ions.

FIG. 1 is a schematic example of a general system 20 for automatically generating chromatography/mass spectrometry spectra, as may be employed in conjunction with the methods of the present teachings. Also, apparatuses in accordance with the present teachings include modifications to the general system 20. As illustrated in FIG. 1, a chromatograph 11, such as, without limitation, a liquid chromatograph, a high-performance liquid chromatograph, an ultra-high-performance liquid chromatograph, a size-exclusion chromatograph or a capillary electrophoresis device, receives a sample 12 of an analyte mixture and at least partially separates the analyte mixture into individual chemical "fractions" or separates, in accordance with well-known chromatographic principles. The chemical compositions of the various eluting fractions or separates differ from one another as a result of the chromatographic separation. The resulting at least partially separated chemical components are transferred to a mass spectrometer 13 at different respective times for mass analysis. As each chemical component is received by the mass spectrometer, it is ionized by an ionization source 14 of the mass spectrometer. The ionization source may produce a plurality of ions comprising a plurality of ion species (i.e., a plurality of precursor ion species) comprising differing charges or masses from each chemical component. Thus, a plurality of ion species of differing respective mass-to-charge ratios may be produced for each chemical component, each such component eluting from the chromatograph at its own characteristic time. These various ion species are mass analyzed by a mass analyzer 15 of the mass spectrometer and detected by a detector 16. As a result of this process, the ion species may be appropriately identified according to their various mass-to-charge (m/z) ratios. As illustrated in FIG. 1, the mass spectrometer comprises a mass filter 17 that is operable to select certain subsets of the precursor ion species according to their m/z values and a fragmentation or reaction cell 18 that is operable to fragment the selected precursor ions, thereby generating a plurality of product ions comprising a plurality of product ion species. The product ions generated by fragmentation of various selected subsets of precursor ion species are also analyzed by the mass analyzer 15 and its associated detector 16.

Still referring to FIG. 1, a programmable processor 19 is electronically coupled to the detector 16 of the mass spectrometer and receives the data produced by the detector 16 during chromatographic/mass spectrometric analysis of the sample(s). The programmable processor 19 may comprise a separate stand-alone computer or may simply comprise a circuit board or any other programmable logic device operated by either firmware or software. Optionally, the programmable processor may also be electronically coupled to the chromatograph 11 and to other various components of the mass spectrometer, as shown by dashed lines, in order to transmit electronic control signals to one or the other of these instruments so as to control their operation. The nature of such control signals may possibly be determined in response to the data transmitted from the detector to the programmable processor or to the analysis of that data as performed by a method in accordance with the present teachings. The programmable processor may also be electronically coupled to a display or other output 22, for direct output of data or data analysis results to a user, or to electronic data storage 23. The programmable processor shown in FIG. 1 is generally operable to: receive a precursor ion chromatography/mass spectrometry spectrum and a product ion chromatography/mass spectrometry spectrum from the chromatography/mass spectrometry apparatus and to automatically perform the various instrument control, data analysis, data retrieval and data storage operations in accordance with the various methods discussed below.

FIG. 2 is a schematic diagram that outlines the general scheme for assessing the quantities of a plurality of target analytes within a sample, according to a conventional LCMS method (e.g., selected reaction monitoring—SRM, or parallel reaction monitoring—PRM). The lowermost curve 1 is a hypothetical elution profile of a single one of the targeted analytes. The indicated time range 2 represents a time period during which the mass spectrometer is directed to acquire scans for a predefined analyte. According to the conventional LCMS method shown, a mass spectrometer continuously acquires MS-n mass spectra for a set of targeted analytes, each within an expected time period when they are expected to elute from the LC (also called time-scheduled acquisition). In order to quantify the concentration of the analyte, the intensity of a set of characteristic fragment ions is integrated over its actual elution time range.

According to the conventional method, the above-noted process repetitively cycles through the various targets. For example, the uppermost portion of FIG. 2 illustrates a set of hypothetical time slices 3a, 3b, where each time slice represents a period of time during which a one of ten different m/z values is mass analyzed. Unshaded time slices 3b represent analysis of the analyte having the elution profile that is shown in the lowermost portion of the figure; shaded time slices 3a represent analysis for the other nine targets. Thus, the particular analyte having the illustrated elution profile is monitored during every tenth time slice, as is schematically illustrated in the central portion of FIG. 2. The gaps between the unshaded time slices reduce the instrument duty cycle that corresponds to the analyte having the elution profile shown in the lowermost portion of FIG. 2. Furthermore, for conventional experiments, it will generally be the case that the actual range of time during which the analyte is analyzed, indicated as the time range 4, will be less than the acquisition segment duration, 2. The reason for this is that, according to conventional run-time scheduling techniques, each target compound is allocated a specific time range 2 during which the instrument acquires mass spectra directed to the compound. The allocated time range is nearly always much greater than the actual time during which the analyte elutes, in order to account for chromatograph drift. This larger time range further reduces the instrument duty cycle that corresponds to the analyte. The same considerations apply to each and every other one of the target analytes.

As suggested in the above paragraph, a disadvantage of the run-time scheduling approach is that the specific elution times of each analyte are subject to drift as the LC column ages, as the LC gradient parameters are changed, and when a new LC column is substituted for an aged one. The elution time drift can lead to the situation that the scheduled windows are no longer aligned with the actual elution times of the analytes, and the collected data are therefore not representative of the abundance of the targeted analytes. The conventional solution to this problem is to utilize over-broad scheduled windows, which reduces the duty cycle of analysis for each analyte. This problem has led to the development of a number of methods to try to correct for elution time drift. One such method is described in co-pending and co-assigned U.S. patent application Ser. No. 16/527,990 titled "Determination and Correction of Retention Time and Mass/Charge Shifts in LC-MS Experiments" that was filed on Jul. 31, 2019. Alternative methods for correcting or compensating for elution time drift are described in the following references:

(a) Sanghvi et. al., "Demonstration of automated on-the-fly retention time updating and SRM method visualization for targeted peptide quantitation". Proceedings of the 64th ASMS Conference on Mass Spectrometry and Allied Topics. San Antonio, Texas, Jun. 5-9, 2016;

(b) Bailey, Derek J., Molly T. McDevitt, Michael S. Westphall, David J. Pagliarini, and Joshua J. Coon. "Intelligent data acquisition blends targeted and discovery methods." Journal of proteome research 13, no. 4 (2014): 2152-2161;

(c) U.S. Pat. No. 9,625,470;

(d) U.S. Pat. No. 10,566,178;

(e) International patent publication WO2017093861 A1;

(f) Gallien et. al., "Highly multiplexed targeted proteomics using precise control of peptide retention time", Proteomics. 2012 April; 12(8):1122-33.

In general, the elution-drift compensation methods rely on the characterization of the elution times of a set of known retention time (RT) standards. These compounds have a wide range of hydrophobicities, such that their elution times span the range of elution times for the analytes of interest. During an analytical experiment, the instrument is directed to periodically monitor for the presence of one or more of the RT standards. When a standard is positively identified, its elution time can be compared to a previous control experiment, and a set of associated analyte windows can be suitably adjusted in real-time.

In order to improve mass spectrometer duty cycles associated with simultaneous quantitative analyses of multiple peptide analytes, Gallien et al. (Gallien, Sebastien, Sang Yoon Kim, and Bruno Domon. "Large-scale targeted proteomics using internal standard triggered-parallel reaction monitoring (IS-PRM)." *Molecular & Cellular Proteomics* 14, no. 6 (2015): 1630-1644) developed a new method called internal standard triggered-parallel reaction monitoring (IS-PRM). The data acquisition scheme described by Gallien et al. employs isotopically labeled internal standards, termed exogenous compounds, each of which is a labeled analog of one of the target analytes. These internal standards are provided for the purpose of readily recognizing the actual elution time ranges of the endogenous analytes, since each internal standard co-elutes with a respective target analyte. Each endogenous analyte and its corresponding exogenous compound comprise a "light ion" and "heavy ion" pair. The IS-PRM method has been modified and adapted from its initial description for commercial implementation under the trade name SureQuant™, which is available from Thermo Fisher Scientific of Waltham, Massachusetts USA. Collectively, the IS-PRM and SureQuant™ methods are herein referred to as the "Internal-Standard-Triggered" mass analysis methods.

According to the IS-PRM method, mass spectrometer data acquisition of each target analyte alternates between two PRM modes: a fast "watch mode" during which the predefined m/z values of the product ions of the exogenous internal standard compound that corresponds to the analyte are watched for and a "quantitative mode" that is triggered when the exogenous compound is actually eluting, based on the detection of its product ions exhibiting expected relative intensities. In the IS-PRM method, the watch mode is active during a "watch time" period prior to elution of analyte. Several such watch time periods may be scheduled over the course of a chromatographic separation, possibly benefiting from a real-time correction from the detected elution time drifts. Only a subset of the total number of exogenous compounds may be watched for during each (dynamically) scheduled watch time period, in accordance with their expected elution times. In the SureQuant™ method, the watch mode is active in each cycle, as indicated in FIG. 3A, relying on MS-1 mass spectra 24, which are constantly acquired using a high-resolution, accurate-mass mass spectrometer, such as an ORBITRAP™ electrostatic trap mass spectrometer. Ions are not fragmented during this watch mode operation. The processing of each MS-1 mass spectrum 24 employs a narrow m/z windows of approximately 10 ppm within which the intensity of expected ion m/z values are extracted. Each such window is chosen to encompass the accurately-known m/z value of the appropriate internal standard. The high mass accuracy of the mass analyzer ensures that background ions are not mistaken for the exogenous compounds. No further ion manipulations, i.e., ion selection and isolation and/or ion fragmentation or reaction, are performed during watch mode operation.

According to the SureQuant™ method, once the target m/z value is detected at an intensity above a predetermined threshold, the mass spectrometer commences execution of an enhanced watch mode of operation, indicated by the time period $\Delta t_W$ in FIG. 3A. During the enhanced watch time period $\Delta t_W$, the Identity of the Compound yielding the target MS-1 signal (as determined by m/z value and intensity of a mass spectral peak) is investigated more closely by means of repetitive MS-2 analyses 25, indicated by squares at various time points along the elution curve 1. During the enhanced watch mode of operation, MS-1 analyses 24, indicated by diamonds, are interspersed with MS-2 analyses 25 of the internal standard. Once a sufficient number of target product m/z values of the exogenous internal standard compound are detected (typically, when at least five out of six target m/z values are detected), the quantitative mode of operation is triggered within the current cycle.

During the SureQuant™ quantitative mode of operation, MS-2 analyses 26 of the endogenous analyte compound, indicated by circles, are interspersed with MS-1 analyses 24 and MS-2 analyses 25 of the co-eluting exogenous internal standard, these analyses being indicated by diamond and squares, respectively. The analyses of the internal standard are used to monitor the progression of the elution in time. The product ions of the labeled internal standard are referred as "heavy" ions whereas the ions of the targeted analyte are referred to as "light" ions. The interspersed MS-1 analyses of internal standard precursor ions and MS-2 analyses of "heavy" and "light" ions continue throughout the time period $\Delta t_2$. Only the elution curve 1 of the endogenous analyte is shown in FIG. 3A; the signal of the exogenous internal standard compound occurs over the same time period and has the same shape but has a much greater magnitude in general. Eventually, the abundance of the exogenous internal standard drops below a certain amount, resulting in a signal intensity of its expected MS-1 ions below a threshold value and/or in the detection of an insufficient number of target product ions, resulting in the non-execution of the enhanced watch mode and/or of the quantitative mode, respectively, and therefore reflecting the end of analyses of the analyte corresponding to elution curve 1. Since the exogenous internal standard is present in the sample at a known concentration, the quantity of the endogenous analyte can be determined by comparison between the integrated signals attributable to the endogenous and exogenous compounds.

By employing gradient elution using slowly-changing chromatographic gradients, the elution times of various analytes of interest can be spread out and mostly separated from one another over an extended period of time. Under such circumstances, the Internal-Standard-Triggered methods advantageously allow efficient mass spectrometric data acquisition of each individual peak, as illustrated in FIG. 3B, since analysis of each analyte is only performed during the specific time period 2 that the analyte elutes. Accordingly, in the ideal case of non-overlapping chromatographic peaks, mass spectrometer data acquisitions that are directed to an m/z value or m/z values that correspond to the eluting analyte are only interspersed with MS-1 analyses of the targeted internal standard compounds and are not interspersed with quantitative data acquisitions that are directed to other compounds. For example, as shown in FIG. 3B, time slices 3b that are directed to mass spectrometer analysis of the analyte having the elution profile 1 occur consecutively (or nearly so) during the time period 5, giving more complete coverage of the full elution time range 2 than is provided by the conventional method (i.e., time range 4 in FIG. 2).

To date, the Internal-Standard-Triggered methods, as described above, have only been implemented on mass spectrometer systems that are capable of high-resolution accurate-mass measurements, such as systems that employ ORBITRAP™ electrostatic trap mass analyzers. Other mass spectrometer systems that employ quadrupole ion trap (QIT) mass analyzers are less costly and more readily available than high-resolution accurate-mass systems. Unfortunately, the lower mass spectral resolution of QIT mass analyzers has been considered to be insufficient for implementation of the SureQuant™ method on systems that employ only such mass analyzers. It has been found that, as a result of this lower mass spectral resolution, execution of the SureQuant™ method on such systems leads to an unacceptably high rate of falsely-triggered MS-2 events, thereby negating any efficiency advantages provided by the method itself. For example, FIG. 4 is a bar chart showing the percentage of false quantitative analysis triggers that are obtained when conducting parallel targeted quantitative analyses, using a quadrupole ion trap mass analyzer and in accordance with the known SureQuant™ method, of the peptides: SSAAPPPPPR; GISNEGQNASIK; HVLTSIGEK; DIPVPKPK; IGDYAGIK; TASEFDSAIAQDK; SAAGAFGPELSR; ELGQSGVDTYLQTK; SFANQPLEVVYSK; GLILVGGYGTR; GILFVGSGVSG-GEEGAR; LTILEELR; NGFILDGFPR; ELASGLSFPVGFK; and LSSEAPALFQFDLK. FIG. 4 shows that, when a QIT-based mass spectrometer system is used to analyze a panel of several standard peptides according to one of these methods, the percentage of false triggers ranges from thirty percent to seventy percent with an average value of fifty percent. The data displayed in FIG. 4 were obtained on labeled peptides included in the Pierce 7×5 System Suitability Test kit, available from Thermo Fisher Scientific of Waltham, Massachusetts USA, after spiking the mixture of standard peptides into a HeLa extract sample at a concentration of 0.4 µg/µL. If one were to perform a routine targeted analysis of eighty peptides by employing the IS-PRM technique on a QIT-based mass spectrometer system, then MS-2 watch scans (corresponding to time period in FIG. 3A) would be triggered fifty percent of the time, on average. Thus, within any given time segment during the watch time period, about forty different falsely-triggered enhanced watch mode MS-2 mass spectral analyses would be ongoing.

Although QIT mass analyzers have poorer mass spectral resolution than is possible with ORBITRAP™ electrostatic trap mass analyzers, they possess a speed advantage relative to those apparatuses. Moreover, practice of the known Internal-Standard-Triggered methods can lead to extended periods of available time, i.e., when no targeted analytes are eluting, during which no useful data is being generated. Thus, if the SureQuant™ method can be improved by adaptation for use with QIT-based mass spectrometer systems in a fashion that reduces the rate of false triggering, such systems may be advantageously employed for rapid targeted mass analyses of multiple peptides.

Although the duty cycle of acquisition of data pertaining to each analyte (e.g., the ratio between the duration of the time period 5 and the duration of the time period 2 in FIG. 3B) may approach one hundred percent, the overall apparatus duty cycle may be much less. Accordingly, a mass spectrometer system that is carrying out IS-PRM targeted analyses may be utilized with even greater efficiency if the time periods between elution peaks of targeted analytes are used to acquire additional useful information. For example, clinical samples and other biologically derived samples may contain various metabolites in addition to peptides. At this time, metabolite databases are not comprehensive even for well-studied tissues and organisms. At the frontiers of research (e.g., metabolome of the microbiome) the number of unknown metabolites (sometimes referred to as "dark matter") that are seen in untargeted LCMS experiments can approach ninety-eight percent (Peisl, Loulou, Emma L. Schymanski, and Paul Wilmes. "Dark matter in host-microbiome metabolomics: tackling the unknowns—a review." Analytica chimica acta 1037 (2018): 13-27". Automated strategies for characterizing the unknowns—especially abundant ones in a tissue or cell population of interest—are called for. Accordingly, it is advantageous to improve the Internal-Standard-Triggered methods so that, in addition to targeted-peptides, various non-targeted compounds may also be analyzed. The non-targeted compounds may be not-targeted peptide compounds, especially peptide compounds that unexpected or unknown, such as peptide compounds that do not have corresponding tabulated entries in a mass spectral library. Such non-targeted compounds may be discovered by means of data-independent mass spectral analyses that are carried out during IS-PRM watch time or survey time periods. The non-targeted compounds may, in some instances comprise classes of compounds other than peptides such as, for example, metabolite compounds. For example, the improved methods may include recognition of the presence of previously uncharacterized "dark matter" metabolite compounds that are not tabulated in any mass spectral library.

SUMMARY OF THE INVENTION

Methods and apparatuses in accordance with the present teachings address the above-noted needs in the mass spectrometry arts by continuously monitoring for the presence of analytes using very fast (but low sensitivity) data independent acquisition (DIA) analyses, and triggering higher sensitivity scans when analytes are detected. According to various methods for the quantification of analytes in accordance with the present teachings, a sample with a set of endogenous analytes to be quantified is mixed with exogenous internal standard (IS) compounds that are isotopically labeled versions of the endogenous analytes. The IS analytes have predictable mass-to-charge ratio (m/z) shifts relative to the endogenous analytes, and the exact same liquid chromatography (LC) elution time profiles. The IS analytes can therefore be added at relatively high concentrations, and used as markers for the elution of endogenous analytes. During LCMS analyses, a mass spectrometer instrument uses unscheduled survey DIA MS-2 analyses to monitor for the presence of the concentrated IS analytes as well as to record the presence of other compounds that may be of interest. The survey DIA analyses utilize wide isolation windows and short dwell times in order to quickly interrogate a large m/z range of ions, as received by a mass analyzer from an ion source.

The monitoring for the presence of the concentrated IS analytes during the survey DIA analyses is done by matching MS-2 spectra to spectral libraries in the form of previously generated spectra or in silico generated spectra. For example, a mass spectral peak-area score may be defined as a mass spectral similarity metric. This metric may be used in combination with one or more other independent mass spectral similarity metrics. Each similarity metric measures an aspect of the degree of overlap between experimental MS-2 results and tabulated values for a standard spectrum in a mass spectral library. The mass spectral peak-area score is a variable that tracks the "intensity" of detection (e.g., number of ions detected per second) of ion species attributable to elution of an internal standard. This score may be calculated as the summation or integration of the raw signal intensity over all m/z values of an MS-2 mass spectrum that are attributable to peaks of internal standard ion species or at which such peaks are expected to appear. The summations may be calibrated in terms of absolute counts of detected ions. When spectra are compared, however, they are typically normalized to a relative scale. The peak-area score and the other mass spectral similarity metrics are herein referred to as "degree-of-matching" scores. When all degree-of-matching scores are evaluated to be above certain threshold values, the instrument is directed to switch its operation to a mode that includes quantitative mass spectral analyses that are directed to measurements of the endogenous analyte and the exogenous IS analyte. These quantitative analyses, which supplement the DIA analyses when the elution of an IS compound is detected, are performed using dwell times that are allowed to be longer than those employed during the survey analyses and using m/z isolation windows that are more selective (i.e., narrower) than those of the survey analyses. These quantitative analyses of exogenous internal standard compounds and endogenous analytes are repeatedly triggered over the entire elution profiles of eluting analytes. Quantitation of each analyte is performed by means of a calculated ratio of the integrated LC peak area for the analyte and its corresponding IS species. In some embodiments, at least some quantitative analyses may take the form of MS-3 analyses, which are more selective than and less susceptible to the presence of interfering species than are MS-2 analyses. In this way, the targeted acquisition of any analyte is only performed within a narrow time window, compared to traditional time-scheduled monitoring windows, which allows the inclusion of more analytes in each experimental run. According to many implementations of the present teachings, the analytes are peptide analytes and, accordingly, the internal standards are isotopically labeled peptides.

Various methods in accordance with the present teachings modify the above-described approach by acquiring only a limited number (ideally just one) of quantitative MS-2 or MS-3 analyses that are directed to simultaneously measuring quantitative signals from both an internal standard (IS) analyte and its corresponding endogenous (ENDO) analyte. Such analyses (or single analysis) are, ideally triggered at the top of each LC chromatographic elution peak for maximum efficiency. According to these variant methods, the ratio of the MS-2 (or MS-3) signals derived from a single analysis or a small number of analyses may be sufficient to quantify an endogenous analyte species. To perform this type of quantitative data acquisition, a quadrupole mass filter (QMF) component of a mass spectrometer is directed to isolate both ion species derived from the exogenous and endogenous analytes with an isolation width of 6-7 Da. Simultaneous isolation of the ion species of both compounds, with the exclusion of ion species of intermediate m/z values, may be achieved, for example, by applying a multi-notch isolation waveform to electrodes of a QMF, or, alternatively, by operating the QMF to separately selectively transmit each ion species to an ion storage apparatus within which the multiple species are accumulated. Simultaneous isolation of multiple ion species may also be performed by appropriate operation of a quadrupole ion trap. The ions of the co-isolated IS/ENDO pair may then be simultaneously fragmented in a first stage of activation. For some accurate-mass analyzers, such as ORBITRAP™ electrostatic trap mass analyzers, the intra-scan dynamic range and mass spectral resolution may be sufficient to use just the ratio of MS-2 signals for quantification. However, increased selectivity may be obtained by further isolating selected MS-2 ion species IS/ENDO pair, fragmenting them, and monitoring the ratio of fragments specific to each analyte.

According to some variations of the present teachings, quantitative analyses that are triggered at or near the top of an LC chromatographic elution peak may be beneficially employed for single-cell proteomics studies. Such studies may make use of endogenous peptide analytes that are labeled by the method known as tandem mass tags (A. Thompson et al., "Tandem Mass Tags: A Novel Quantification Strategy for Comparative Analysis of Complex Protein Mixtures by MS/MS", Anal. Chem. 2003, 75, 1895-1904). Analytes that are labeled by the tandem mass tag (TMT) technique include a mass reporter region, a cleavable linker region, a mass-normalization region and a reactive group. Different samples of a single peptide, when labeled with different respective tandem mass tag (TMT) reagents, will all comprise the same chemical structure and mass and will therefore co-elute. Upon mass spectrometric analysis of a TMT-labeled compound by collision-induced dissociation, an ion is released that has a specific mass-to-charge ratio that is diagnostic of a specific tag, thereby enabling identification of the source of the peptide or protein. During the mass analysis, precursor ions comprising particular m/z ratios corresponding to expected or known peptides are isolated. These precursor ions are then fragmented by collision-induced dissociation so as to both cleave the peptide backbone as well to fragment the labeled tags. In accordance with the present teachings, DIA can be used to monitor the presence of an appropriate internal standard for a TMT-labeled analyte, and thereby trigger analysis at an m/z corresponding to the analyte. Analysis, via MS-2 or MS-3, of these compounds leads to the generation of reporter ions, the relative intensities of which are used to quantitate the analytes.

In accordance with a first aspect of the present teachings, a method for determining a quantity of a analyte in a liquid sample, comprises: (a) adding a known quantity of an internal standard comprising an isotopically labeled version of the analyte of interest to the sample; (b) providing a continuous stream of the sample having the internal standard to an inlet of a Liquid Chromatography Mass Spectrometry (LCMS) system comprising a liquid chromatograph fluidically coupled to a mass spectrometer, whereby the liquid chromatograph separates the stream into chemical separates that are received by and ionized by the mass spectrometer, the ionization generating a plurality of precursor ion species; and (c) repeatedly performing the steps of: (c1) performing a data-independent analysis of the precursor ion species using a mass analyzer, whereby mass spectra of a plurality of product-ion species generated by fragmentation of the precursor ion species are acquired; (c2) calculating one or more degree-of-matching scores that relate to either a number of ions of the internal standard or to the overlap between results of the data-independent analysis and tabulated mass spectral data of the internal standard; and (c3) performing a quantitative tandem mass spectrometric analysis of the internal standard and a quantitative tandem mass spectrometric analysis of the endogenous analyte if each of the degree-of-matching scores meets a respective degree-of-matching condition; and (d) calculating the quantity of the analyte in the sample by comparison between intensities of one or more mass spectral signals generated by the quantitative analyses of the endogenous analyte to intensities of one or more mass spectral signals generated by the quantitative analyses of the internal standard.

BRIEF DESCRIPTION OF THE DRAWINGS

The above noted and various other aspects of the present invention will become apparent from the following description which is given by way of example only and with reference to the accompanying drawings, not necessarily drawn to scale, in which.

DETAILED DESCRIPTION

Figure 1:
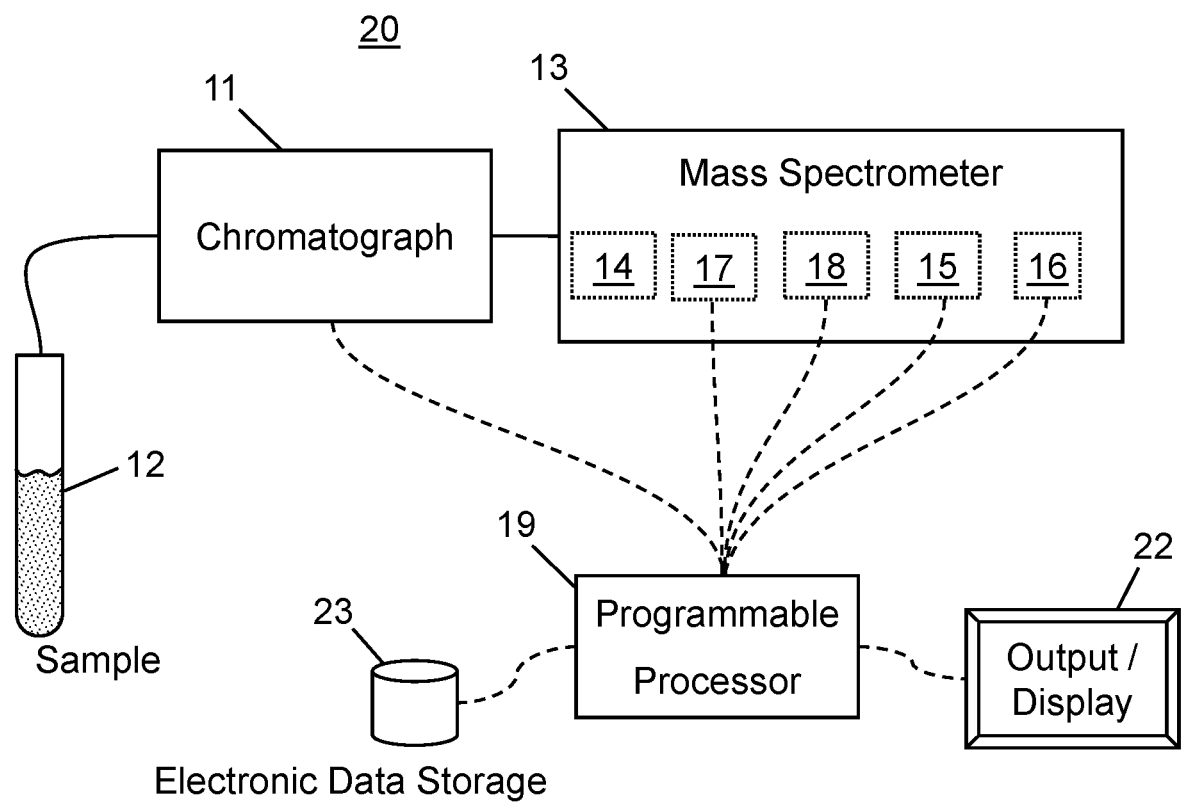
FIG. 1 is a schematic general depiction of a Liquid Chromatography Mass Spectrometry (LCMS) analytical system.
Figure 2:
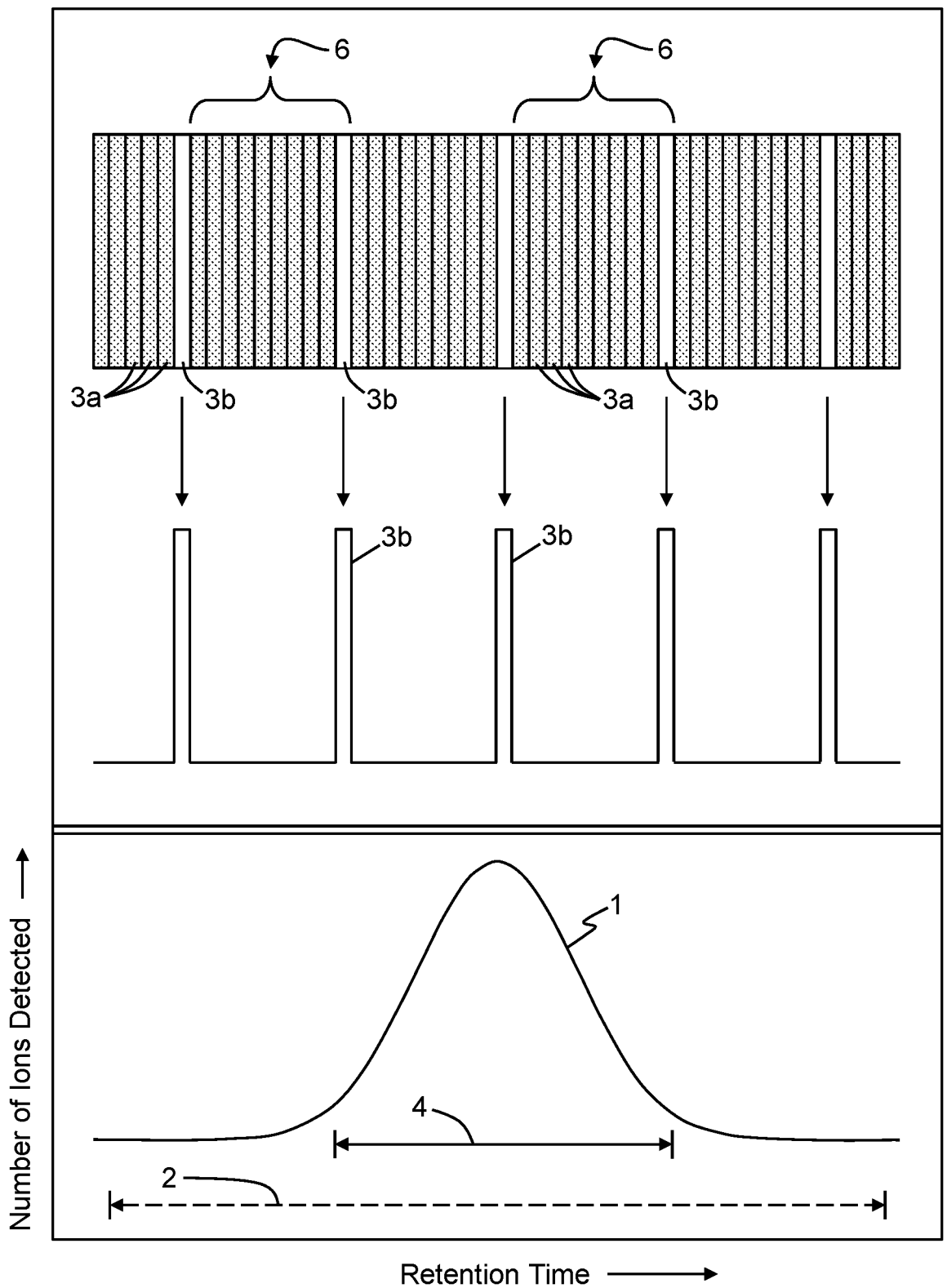
FIG. 2 is a schematic diagram outlining a general scheme for assessing the quantities of a plurality of target analytes within a sample, according to a conventional targeted LCMS method (e.g., a time-scheduled acquisition)
Figure 3A:
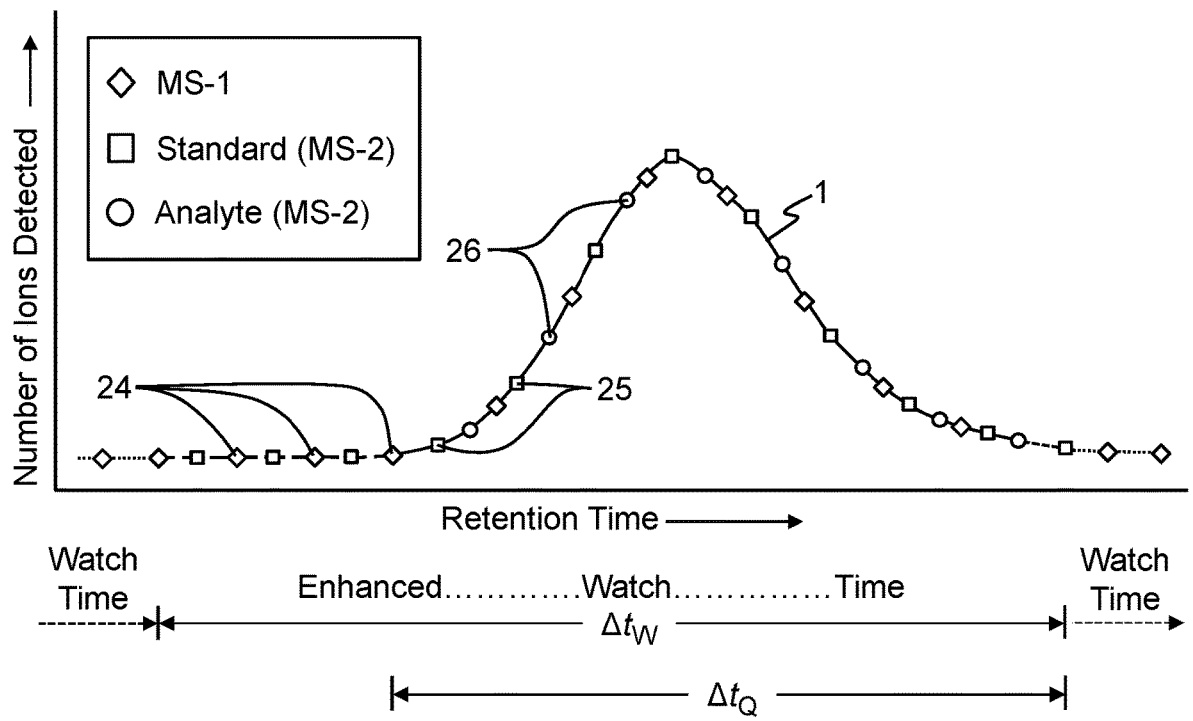
FIG. 3A is a schematic illustration of a sequence of mass spectrometer analysis events that may occur over the course of elution of a hypothetical targeted analyte that is being quantitatively analyzed using the SureQuant™ technique.
Figure 3B:
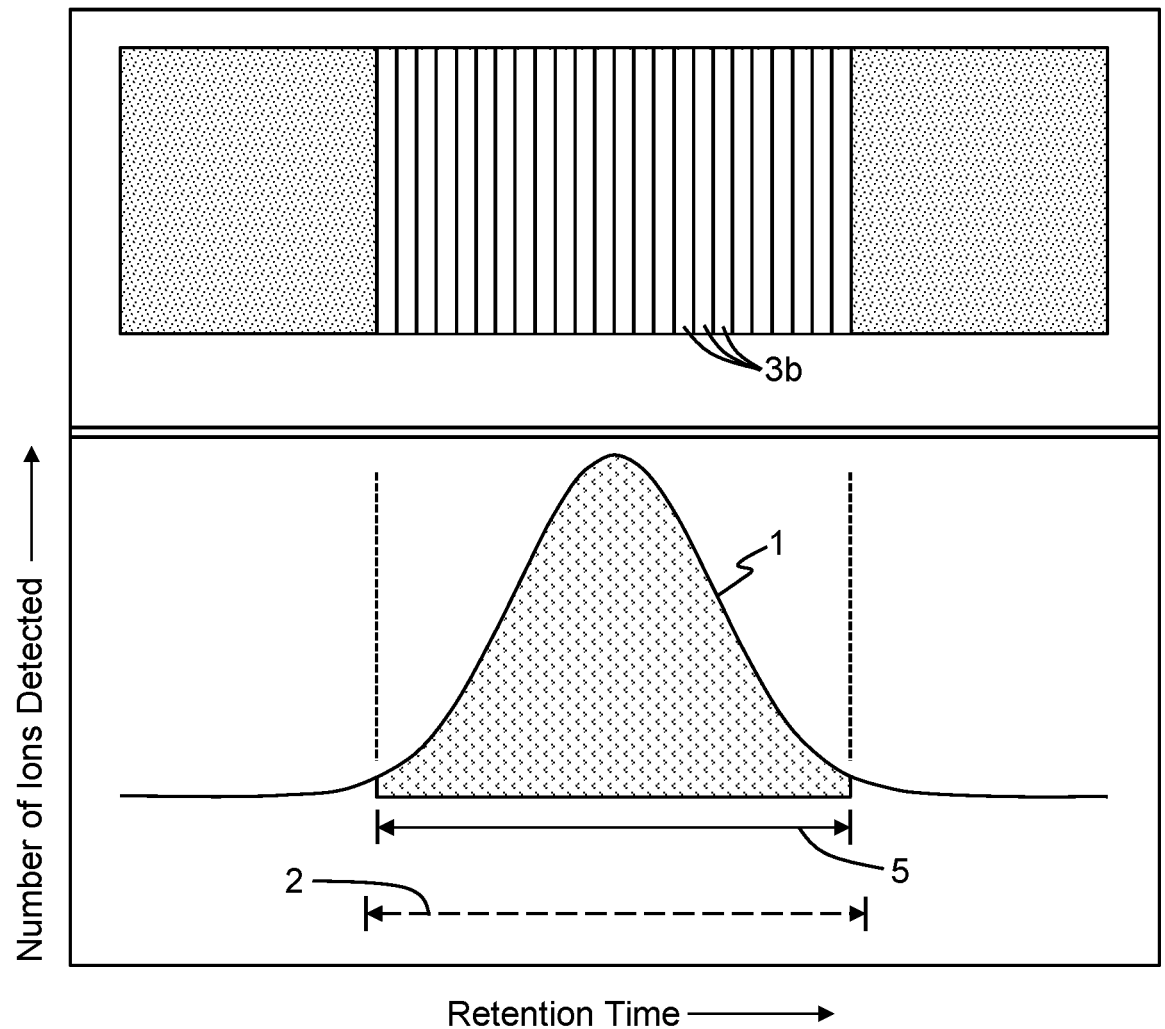
FIG. 3B is a schematic illustration of hypothetical mass spectrometer analytical coverage of a chromatographic elution peak over the course of elution of a hypothetical targeted analyte that is being quantitatively analyzed using one of the known Internal-Standard-Triggered quantitative analysis techniques.

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. To fully appreciate the features of the present invention in greater detail, please refer to FIGS. 1, 2, 3A-3B, 4, 5A-5B, 6, 7A-7B, 8A-8B, 9, 10A-10B, 11A-11B, 12-15, 16A and 16B in conjunction with the following description.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that, for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise.

As used in this document, the term "scan", when used as a noun, means a mass spectrum, regardless of the type of mass analyzer used to generate and acquire the mass spectrum. When used as a verb herein, the term "scan" refers to the generation and acquisition of a mass spectrum by a method of mass analysis, regardless of the type of mass analyzer or mass analysis used to generate and acquire the mass spectrum. As used herein, the term "full scan" refers to a mass spectrum than encompasses a range of mass-to-charge (m/z) values that includes a plurality of mass spectral peaks. As used herein, the term "MS-1" refers to either a mass spectrum or the generation and acquisition of a mass spectrum that pertains to ions received by a mass analyzer from an ion source, including any ions that may have been modified from their initial states by in-source fragmentation. As used herein the term "MS-2" refers to either tandem mass spectrometry or a result obtained by the technique of tandem mass spectrometry, as described above. As used herein, the term "MS-3" refers to a technique in which: (a) certain fragment ions, generated in a fragmentation or a reaction cell, are selected, isolated and subsequently themselves fragmented in a fragmentation or a reaction cell, thereby generating fragments of fragment ion species; and (b) the fragment ion species resulting from execution of the steps of (a) are mass analyzed. As used herein, the term "MS-3" may also refer to a result obtained by execution of the MS-3 technique.

As used in this document, each of the terms "liquid chromatograph" and "liquid chromatography" (both abbreviated "LC") as well as the term "Liquid Chromatography Mass Spectrometry" (abbreviated as either "LCMS" or "LC-MS") are intended to apply to any type of liquid separation system that is capable of separating a multi-analyte-bearing liquid sample into various "fractions" or "separates", where the chemical composition of each such "fraction" or "separate" is different from the chemical composition of every other such fraction or separate, wherein the term "chemical composition" refers to the numbers, concentrations, and/or identities of the various analytes in a fraction or separate. As such, the terms "liquid chromatograph", "liquid chromatography" "Liquid Chromatography Mass Spectrometry", "LC", "LCMS" and "LC-MS" are intended to include and to refer to, without limitation, liquid chromatographs, high-performance liquid chromatographs, ultra-high-performance liquid chromatographs, size-exclusion chromatographs and capillary electrophoresis devices.

Unless otherwise defined, all other technical and scientific terms used herein have the meaning commonly understood by one of ordinary skill in the art to which this invention belongs. In case of conflict, the present specification, including definitions, will control. It will be appreciated that there is an implied "about" prior to the quantitative terms mentioned in the present description, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. As used herein, "a" or "an" also may refer to "at least one" or "one or more." Also, the use of "or" is inclusive, such that the phrase "A or B" is true when "A" is true, "B" is true, or both "A" and "B" are true.

Figure 5A:
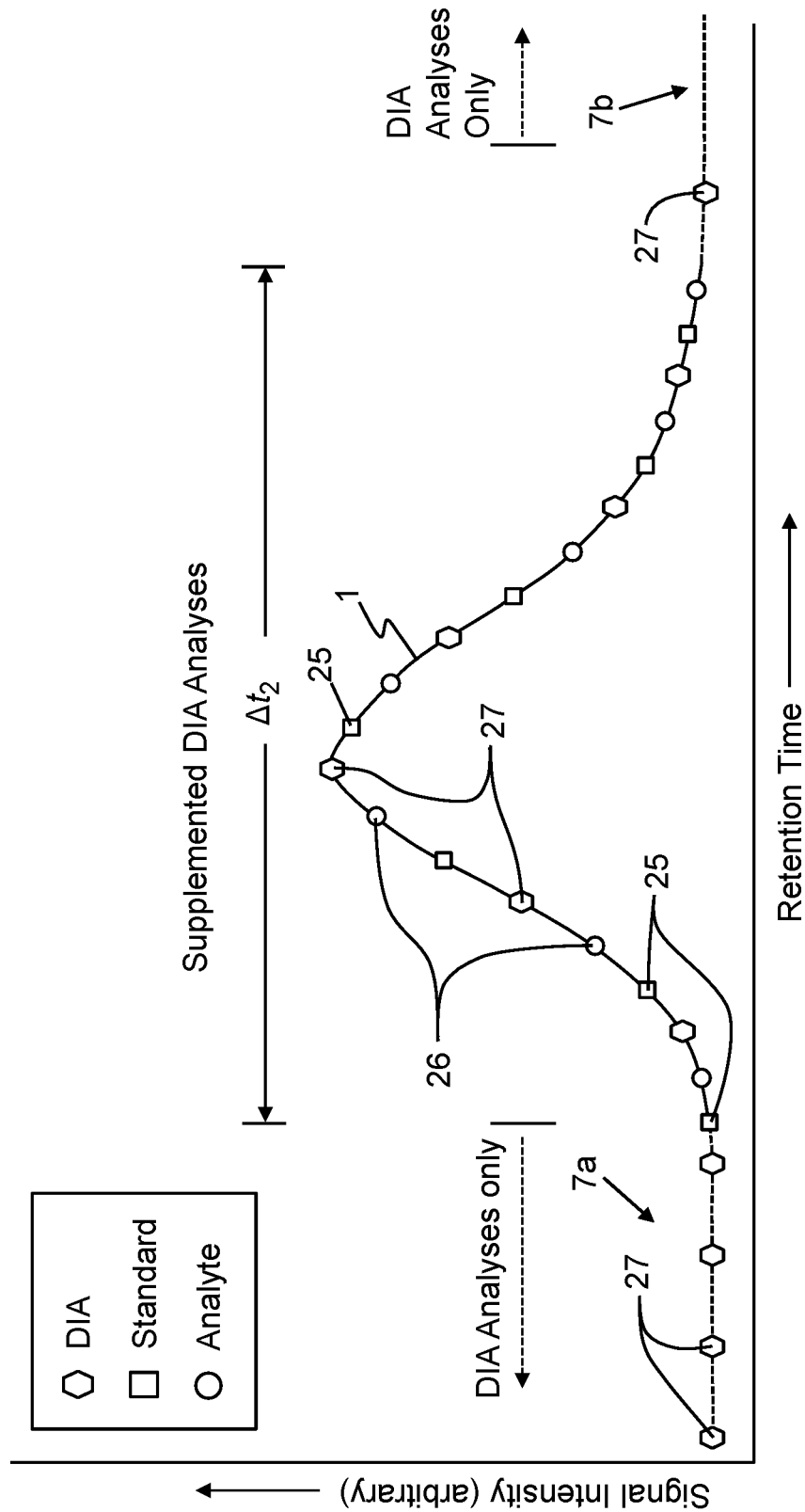
FIG. 5A is a schematic illustration of a sequence of mass spectrometer analysis events that may occur over the course of elution of a hypothetical targeted analyte that is being quantitatively analyzed according to a method in accordance with the present teachings.
Figure 5B:
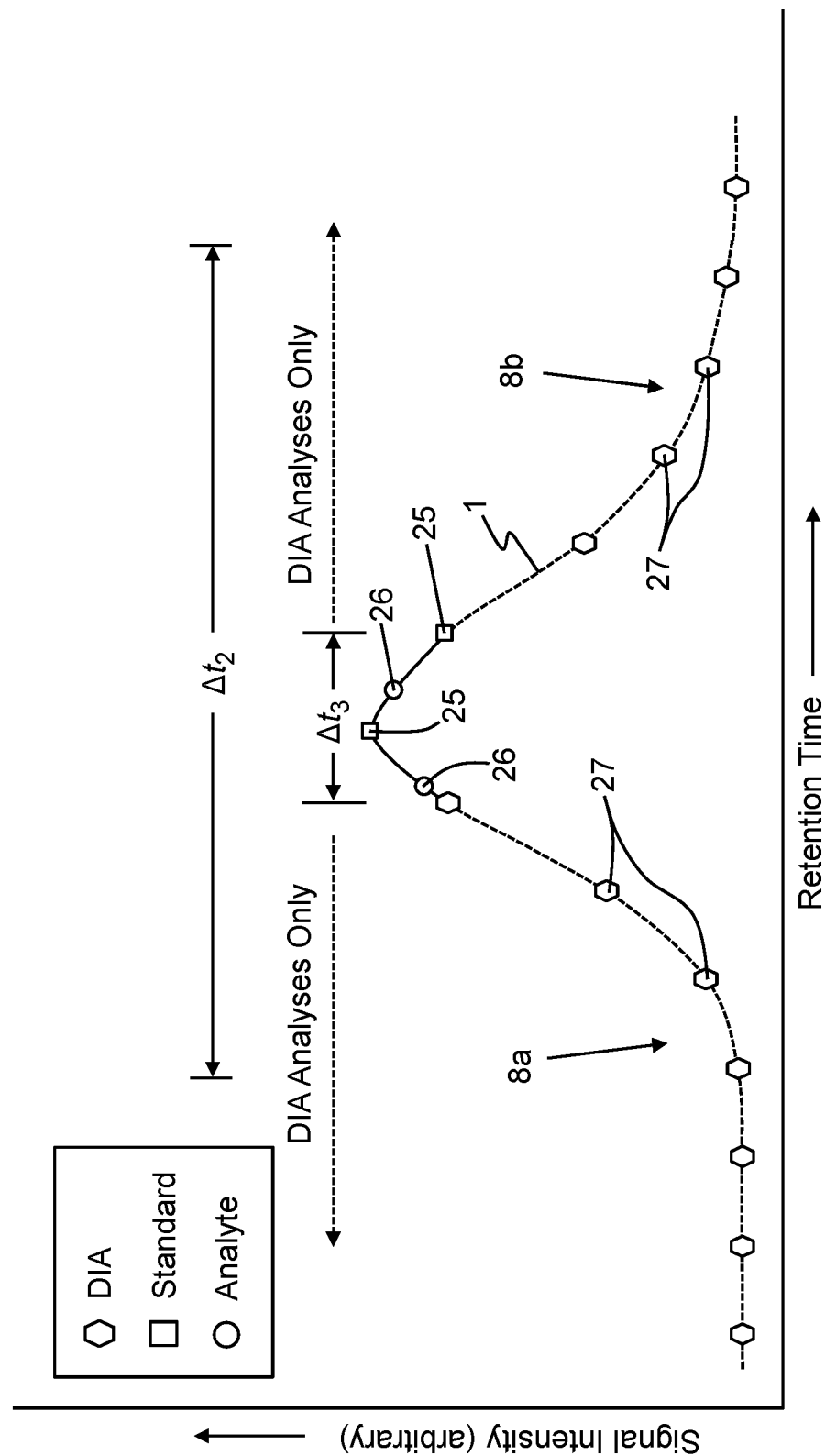
FIG. 5B is a schematic illustration of a sequence of mass spectrometer analysis events that may occur over the course of elution of a hypothetical targeted analyte that is being quantitatively analyzed according to another method in accordance with the present teachings.

FIGS. 5A and 5B are schematic illustrations of sequences of mass spectrometer analysis events that may occur over the course of elution of a hypothetical targeted analyte that is being quantitatively analyzed according to a first method and a second method, respectively, in accordance with the present teachings. In general, the analysis methods in accordance with the present teachings employ an operational mode (i.e., a mass spectral survey mode) that comprises a series of rapidly repeated data-independent analyses. These data-independent analysis (DIA) mass spectral measurements comprise both MS-1 and MS-2 analyses which are acquired using short dwell times and large MS-2 isolation windows in order to decrease the amount of time needed to characterize a given range of precursor mass-to-charge values. An example of DIA analysis is described in more detail below with reference to FIG. 6. The set of DIA survey measurements generate a nearly continuous record of exogenous internal standard compounds, endogenous targeted analyte compounds, matrix compounds and other sample-derived compounds as they emerge from the outlet of a liquid chromatograph. Such operation, as taught herein, is in contrast to the SureQuant™ technique, discussed above, in which only MS-1 scans are relied upon, without any ion isolation or fragmentation, during watch mode operation in order to detect the onset of exogenous internal standard elution. The DIA survey analyses that are utilized by methods in accordance with the present teachings are able to provide rich information regarding the chemical constitution of a sample. This information may be employed to not only determine the onset of elution of the internal standards but also to detect and identify metabolite compounds in a sample, to record the presence of so-called dark matter compounds within the sample and to detect and compensate for retention time drift during the course of experiments.

As shown FIG. 5A, only DIA analyses are executed during a time period $7a$ prior to the detected onset of elution of the first-eluting exogenous internal standard having the elution profile 1. It should be kept in mind that, although only a single elution profile 1 is illustrated in FIGS. 5A-5B, each endogenous targeted analyte co-elutes with its corresponding internal standard compound, with the two elution profiles occurring over the same time range, $\Delta t_2$ and having the same shape but different magnitudes.

The DIA scans 27 that are executed during time period $7a$ include numerous MS-2 analyses. The MS-2 analyses are used to monitor for the presence of the various exogenous internal standard peptides. At every cycle of the DIA analyses, one or more degree-of-matching scores are calculated, each of which is a measure of either the intensity of an observed mass spectral signal attributable to a specific internal standard (IS) compound or the degree of overlap between a standard spectrum and observed peaks of the experimental MS-2 results, where each standard spectrum relates to a specific IS compound. When all degree-of-matching scores exceed their respective predetermined threshold values, thereby indicating elution of an exogenous internal standard compound, then additional quantitative scans are triggered. In some instances, only one degree-of-matching score may be utilized for triggering the additional quantitative scans. For example, the additional quantitative scans may be triggered when only a peak area score that is attributable to an internal standard is above a threshold value. Conveniently, the threshold value for the peak area score may be set within the range of 1-5 percent of an expected maximum value, where the expected maximum value is the value of the peak area score anticipated at the apex of an elution peak 1.

The first instance at which a score that relates to a particular IS compound exceeds the threshold initiates a second mode of mass spectral operation, here referred to as a supplemented DIA analysis mode, an example of which is shown within time range, $\Delta t_2$ in FIG. 5A. In the supplemented DIA analysis mode, DIA analyses 27 continue and are supplemented by a first set and a second set of additional quantitative MS-2 analyses. The first set of additional quantitative MS-2 analyses 25 are directed to measurement of the detected exogenous internal standard compound. The second set of additional quantitative MS-2 scans 26 are directed to the measurement of the targeted endogenous analyte that corresponds to the detected internal standard compound. During the time period $\Delta t_2$, degree-of-matching score(s) are calculated for each DIA analysis 27 as well as for each internal standard analysis 25 that is triggered from a DIA analysis. Each time that all degree-of-matching scores from a DIA analysis are above their respective threshold values, a subsequent pair of analyses, comprising an internal standard analysis 25 and an analyte analysis 26 are triggered.

Once any degree-of-matching score, as calculated from the MS-2 analysis of the internal standard has dropped below a threshold value (typically at the end of the elution time period), then a subsequent instance of DIA-only survey mode operation may ensue during time period 7b, provided that no other targeted analytes are eluting. The DIA survey scans 27 that are interspersed with the internal standard analyses 25 and targeted analyte analyses 26 are used to detect the commencement of elution, if any, of a second, different exogenous internal standard compound during the time range, $\Delta t_2$. If such elution is detected, then additional MS-2 analyses (not specifically shown in FIG. 5A) are executed that are directed to that second internal standard compound and to its respective corresponding endogenous targeted analyte. In the event that interfering noise in any one of the DIA analyses 27 causes an accidental failure to trigger the quantitative analyses 25 and 26, then such quantitative analyses will nonetheless still be triggered provided that the degree of matching score(s) for the most recent internal standard analysis 25 is/are above threshold. Thus, a pair of quantitative analyses 25 and 26 will be triggered if an above-threshold degree-of-matching score (or scores) is/are observed for either the most recent DIA analysis 27 or the most recent internal standard analysis 25.

FIG. 5B is a schematic illustration of sequences of mass spectrometer analysis events as may occur in accordance with an alternative method of operation of the present teachings. Compared to the sequence of events that is depicted in FIG. 5A, the time range, $\Delta t_3$, during which quantitative analyses of an analyte and its respective internal standard are obtained is reduced in length relative to the total effective elution time, $\Delta t_2$. According to the sequence of events shown in FIG. 5B, the time period utilized for quantitative analysis of each analyte and its respective exogenous internal standard is restricted to a narrow range in the vicinity of the analyte's elution peak apex. Restriction of the quantitative analysis period in this fashion is possible if each exogenous internal standard is present in the sample at a concentration that is sufficient to yield a high signal-to-noise ratio in its mass spectrometric signal and if the general form and expected magnitude of the signal is known or can be reliably estimated in advance of experimental measurements. Under such conditions, the initiation of quantitative analyses of an analyte and its respective exogenous internal standard may be delayed until the magnitude of the IS signal intensity (e.g., as tracked by a peak-area score) exceeds a predetermined percentage of its expected maximum value. Also, cessation of a series of quantitative analyses of the analyte and its respective internal standard may occur when the magnitude of the IS signal intensity subsequently drops below the predetermined percentage.

For example, to restrict the time range that is allotted for quantitative analysis of each targeted analyte to the depicted narrow time range, $\Delta t_3$, surrounding the apex of the elution peak, a threshold that should be met by a mass spectral peak-area score in order to trigger the analyte analysis may be set at seventy-five percent of an expected maximum value, at the top of an elution peak. Less preferably, the threshold may be set at fifty percent, or within the range of twenty-five to thirty percent of the expected maximum value. The lower thresholds may be used to take into account time delay between detection and actual acquisition in experiments that include a very large number of targets. Alternatively, the initiation of quantitative analyses of an analyte and its respective internal standard may be delayed until the IS signal stops increasing and begins to decrease. In such instances, the quantitative analyses may be limited to just a single analysis of each of the analyte and its respective internal standard at the top of the elution peak. These procedures may be accomplished by numerically monitoring the rate of change of the mass spectrometer signal across the elution peak. There are various existing methods for estimating when the apex of a peak has been reached (for example, see U.S. Pat. No. 7,943,899, which is commonly assigned with the present application), any of which may be employed in conjunction with the methods of the present teachings. Regardless of which peak apex identification method is used, the concentration or quantity of the endogenous analyte in the sample is determined from the ratio of the separate integrated signals pertaining to internal standard and endogenous analyte at or near the apex.

Restriction of the time range, Y, that is allotted for quantitative analysis of each targeted analyte, as shown in FIG. 5B, allows expansion of the time ranges, 8a and 8b, that are allotted for DIA and targeted analyses of other analytes, thereby improving the efficiency of use of an LCMS system. The additional DIA analyses that are enabled through reduction of the time allotted to quantitative analyses may be used to more completely characterize the full range of peptides and other compounds, such as biological metabolites, that may be present in a sample. For greatest efficiency, the quantitative analyses pertaining to a particular targeted peptide analyte are ideally limited to just a single MS-2 analysis of the endogenous analyte and a single MS-2 analysis of the analyte's corresponding endogenous internal standard, both taken near the maximum of the elution profile 1. In some instances, selected precursor ions of the analyte and internal standard may be co-isolated, in the essential absence of other ion species, and simultaneously fragmented to yield a mixture of fragment ions generated from essentially only the selected ion species. This procedure can allow the information relating to fragments of both the analyte and internal standard to be contained within a single mass spectrum, thereby further improving the efficiency of use of an LCMS system.

In some instances, co-isolation of selected precursor ions may be achieved by applying a broadband resonance ejection frequency waveform to an ion trap, wherein the waveform comprises multiple summed sinusoidal frequency components, wherein included frequency components corresponding to the m/z ranges of ions that one desires to eject from the trap and excluded frequency components correspond to the m/z range of ions that one desires to retain within the trap. In this procedure, the omitted frequencies define one or more frequency notches in the ejection frequency waveform. The frequency components may be calculated by first choosing a desired multi-notch waveform and then calculating an inverse Fourier Transform of the desired waveform. In other instances, the co-isolating of the subset of the plurality of first-generation product ion species may be performed by isolating individual precursor ion species in a conventional sense, one ion species at a time using either a quadrupole mass filter or an ion trap operated conventionally, and transferring each individually isolated ion species to a fragmentation cell or to an ion storage component in which the various selected and isolated ion species are accumulated as a mixture of ions.

Figure 6:
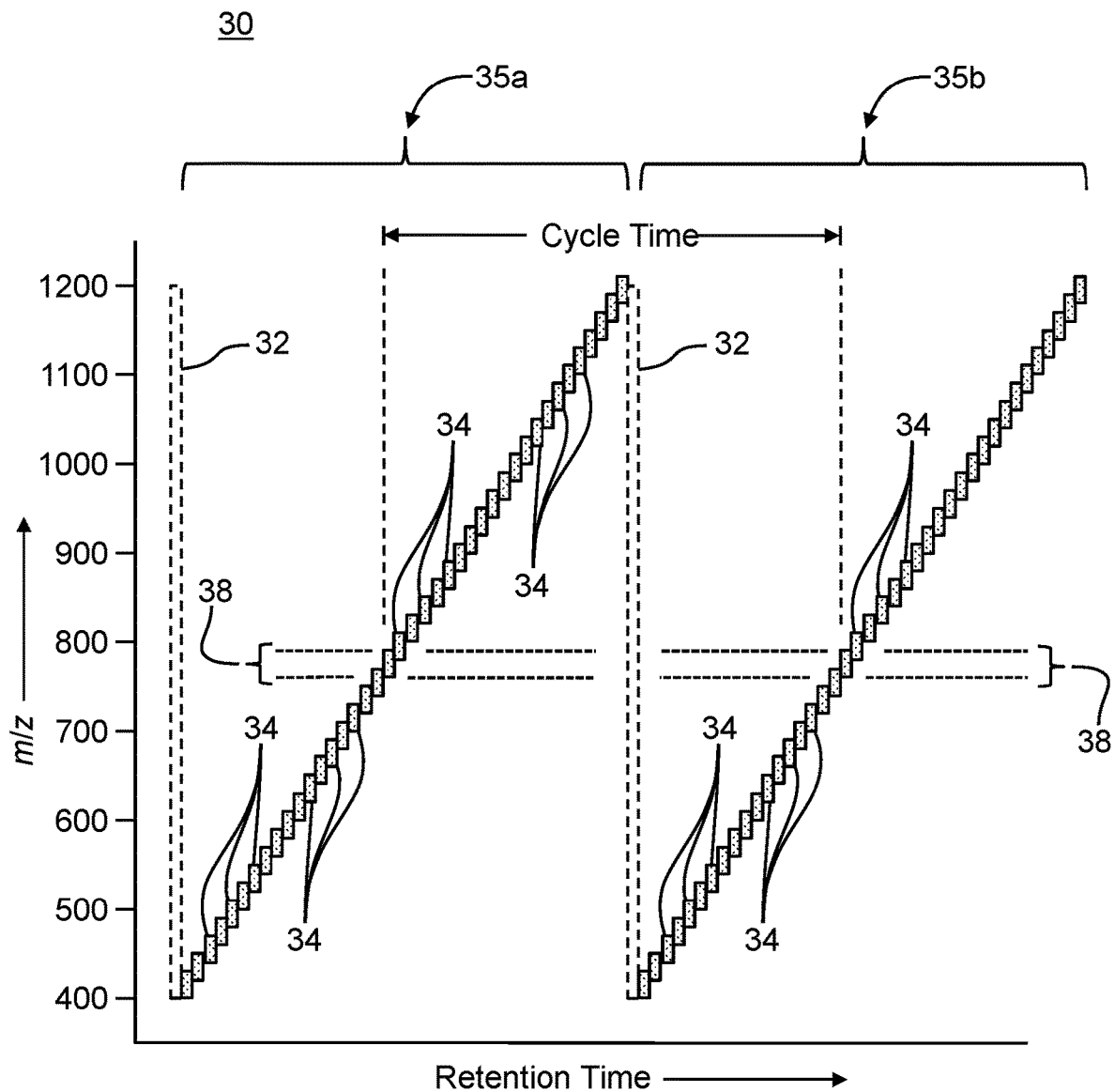
FIG. 6 is a highly schematic diagram illustrating the general sequence of events that may occur during a hypothetical LCMS analysis performed according to a known data-independent acquisition method that is referred to as "SWATH MS"

FIG. 6 is a highly schematic diagram, shown generally at 30, illustrating the general sequence of events that may occur during a hypothetical LCMS analysis performed according to one data-independent acquisition method known as "SWATH MS" (Gillet et al., Targeted Data Extraction of the MS/MS Spectra Generated by Data-independent Acquisition: A New Concept for Consistent and Accurate Proteome Analysis, Mol. Cell. Proteomics, 2012, 11(6): O111.016717. DOI: 10.1074/mcp.O111.016717). In the diagram shown in FIG. 6, m/z values of precursor ions or first-generation ions are represented as ordinate values and chromatographic retention time values are represented as abscissa values. The SWATH MS data-independent procedure includes consecutively acquiring a series of high-resolution, accurate-mass fragment-ion spectra (i.e., MS-2 spectra) during an entire chromatographic elution (retention time) range by repeatedly stepping through a number (for example thirty two) of discrete precursor-ion isolation windows of a certain width (for example, 25 Da width) across a full mass spectral range of interest (for example, the 400-1200 m/z range). Thus, a main feature of the technique, as illustrated in FIG. 6, is a plurality of series of consecutive product-ion analyses 34. Each such product ion analysis 34 is represented as a shaded box and includes the steps of: isolation of precursor ions within a restricted range of precursor-ion m/z values as indicated on the ordinate, fragmentation of the isolated precursor ions so as to generate fragment ions and mass analysis of the fragment ions generated from the isolated precursor ions. Each restricted range of precursor m/z values may be termed an "isolation window" (or, equivalently, an "isolation range" or an "isolated range") and is represented by the range of ordinate values that is spanned by a respective one of the boxes 34. The width of the isolation windows (height of the boxes 34) is significantly greater than those of isolation windows employed in conventional targeted analytical methods and are represented, in FIG. 6, by the height of the shaded boxes that represent the product ion analyses. It should be noted that the product ions, themselves, that are generated by fragmentation of set of precursor ions may comprise a different range of product-ion m/z values (not specifically indicated by any box).

Two series, 35a and 35b, of product-ion analyses are illustrated in FIG. 6. Consecutive isolation windows (corresponding to consecutive product-ion analyses) may partially overlap one another in m/z to assure that there are no m/z gaps within which m/z positions of unfragmented first-generation ions occur. Once the series of isolation windows has covered the full m/z range of interest (i.e., once an end of the full m/z range of interest has been reached), then a new series of consecutive product-ion analyses is investigated in similar fashion starting at the opposite end of the range. The boxes 32 outlined with dashed lines at the beginning of each cycle depict optional acquisition of a high-resolution, accurate mass survey scan of precursor ions throughout the full m/z range of interest. The totality of data product-ion analyses 34 corresponding to any given precursor mass range across the range of retention times is oftentimes referred to as a "swath". One such swath is shown at 38 in FIG. 6.

Figure 7A:
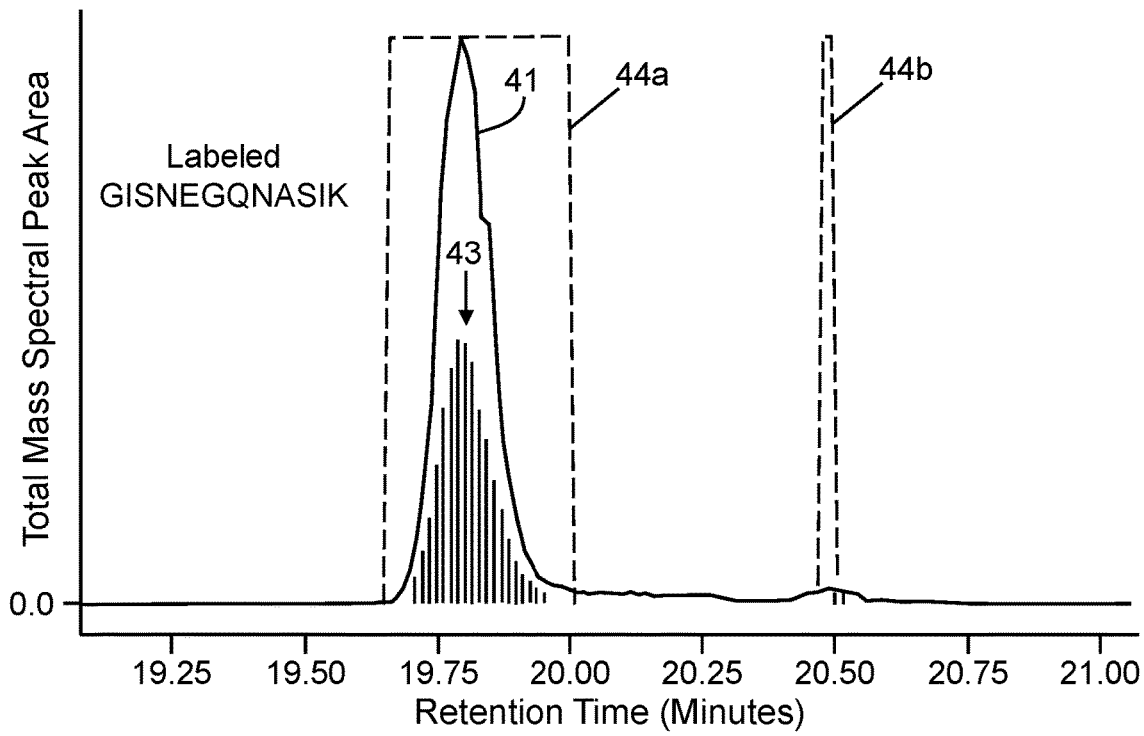
FIG. 7A is a graphical plot of mass spectrometer signals, which are reported as total mass spectral peak area, versus retention time, in minutes, the mass spectrometer signals being generated in accordance with the present teachings, acquired during elution of a labeled version of the peptide GISNEGQNASIK.
Figure 7B:
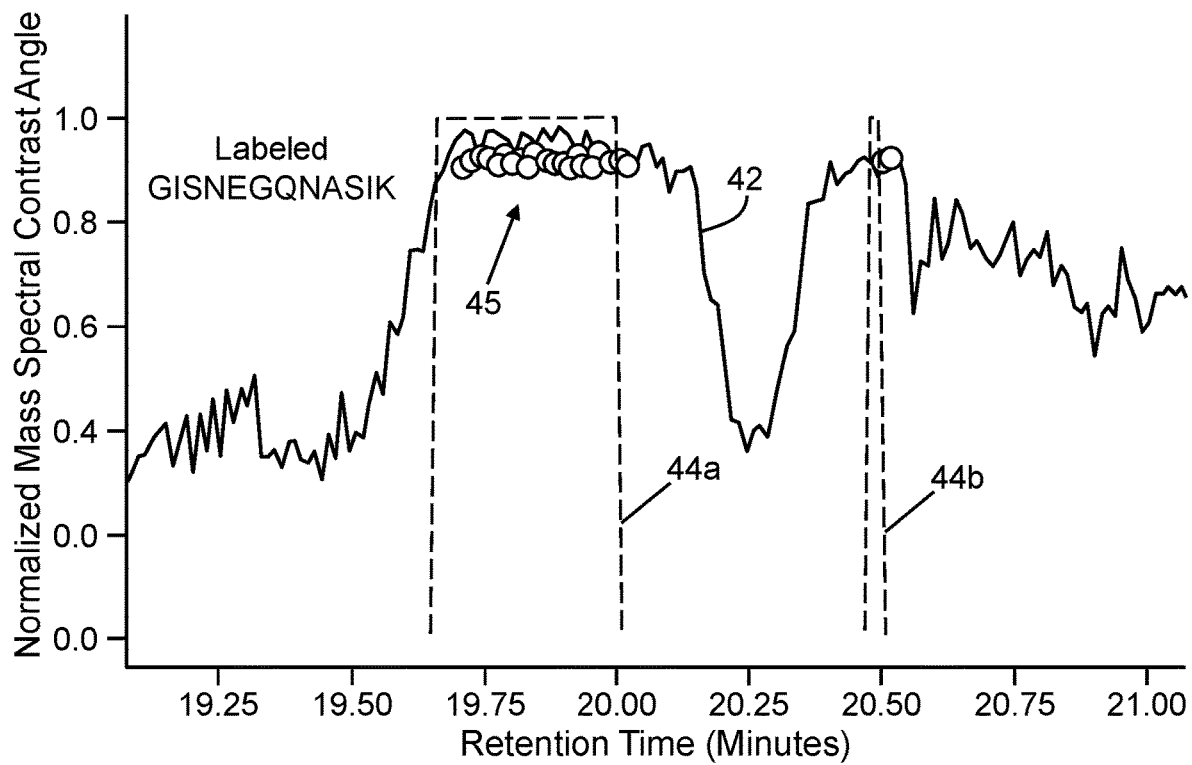
FIG. 7B is a graphical plot of normalized mass spectral contrast angle versus Retention Time, in minutes, the mass spectral contrast angles being as determined during quantitative mass analysis conducted in accordance with the present teachings during elution of a labeled version of the peptide GISNEGQNASIK.

FIGS. 7A-7B illustrate details of a procedure, in accordance with the present teachings, for triggering quantitative analyses. Generally, triggering occurs when all calculated degree-of-matching scores satisfy respective degree-of-matching conditions, where each such score is a measure of similarity of experimental MS-2 results to a data entry in a mass spectral library. Both FIG. 7A and FIG. 7B pertain to LCMS analysis, performed in accordance with the present teachings, of the peptide having amino acid sequence GIS-NEGQNASIK. The data illustrated in FIGS. 7A-7B are the results of tests of the reliability and consistency of triggering of quantitative analyses, as performed in accordance with the present teachings. The mass spectral analyses whose results are depicted in FIGS. 7A-7B, as well as in FIGS. 8A-8B and FIG. 9, were obtained from aliquots of the Pierce Retention Time Calibration (PRTC) mixture, which is commercially available from Thermo Fisher Scientific of Waltham, Massachusetts USA. This product is an equimolar calibration mixture that contains fifteen heavy-isotope-labeled peptides with each peptide present at a concentration of 0.5 pmol/µL. In the present studies, the PRTC peptides were spiked into a HeLa digest sample to yield final peptide concentrations of 100 fmol/µl. Triggering of quantitative analyses of the analyte was performed by methods in accordance with the present teachings as described in greater detail below.

FIG. 7A is a pair of plots of experimentally measured integrated MS-2 peak area, with trace 41 indicating the determined integrated peak area of the internal standard proxy as a function of retention time and bar chart 43 indicating the determined integrated peak area for the analyte proxy as a function of retention time. The position of each bar in bar chart 43 indicates a retention time at which measurement of the analyte was triggered based on the detection of corresponding internal standard peptide. FIG. 7B is a plot 42 of a normalized form of spectral contrast angle, $\theta$, where $\theta$ is defined by $$\theta = \cos^{-1}\left(\frac{\sum_i a_i b_i}{\sqrt{\sum_i a_i^2 \sum_i b_i^2}}\right) \quad \text{Eq 1}$$

where $a_i$ and $b_i$ are the relative intensities of product-ion peaks at the $i^{th}$ value of m/z for the exogenous compound and the corresponding mass spectral library entry, respectively.

According to some methods of the present teachings, a quantitative MS-2 analysis is triggered only at those times when both the observed integrated peak area (i.e., integration over the mass-to-charge variable), $A_{2s}$ relating to the internal standard and the determined spectral contrast angle, $\theta$, meet their respective threshold value conditions. The threshold conditions may be explicitly stated as follows:

$$A_{2S} > t_{AREA} \text{ and } \theta > t_\theta \quad \text{Eqs. 2}$$

where $t_{AREA}$ and $t_\theta$ are the area and spectral contrast angle thresholds, respectively. These conditions may apply to triggering based on results of either a DIA analysis 27 or an analysis 25 of an exogenous internal standard.

In FIGS. 7A and 7B, dashed outlines 44a and 44b indicate regions in which quantitative scans were automatically triggered in accordance with the above-noted conditions. The retention times and $\theta$ values of individual triggered quantitative analyses of the internal standard are indicated by circles 45 in FIG. 7B; the positions of individual triggered analyses are also indicated by the positions of the bars of bar chart 43 of FIG. 7A. As may be observed from FIGS. 7A-7B, most trigger events occur within and throughout the correct analyte elution period between the lower retention time of approximately 19.65 minutes and the upper retention time of 20.04 minutes. However, two false trigger events were observed at a retention time of approximately 20.50 minutes. These may be recognized as false triggers either by increasing the area threshold value, $t_{AREA}$, (observing that the chromatograph peak at retention time 20.50 minutes is too weak), by rejecting the false triggers based on their outlier status or by adding an additional retention time criterion to the list of degree-of-matching conditions.

One potential factor that may contribute to the occurrence of false triggers when performing a sequence of DIA analyses is the width, in m/z in units of thomsons, Th, of the isolation windows that are used to select groups of precursor ions for fragmentation. (Note that such isolation window widths are schematically represented by the height of the rectangles representing product ion analyses 34 in FIG. 6.) When performing a set of targeted quantitative analyses in accordance with the present teachings, it may be desirable to set an optimal isolation window width beforehand. A narrow isolation width, such as a width of 4 Th, yields reasonably good selectivity, since fewer potentially interfering non-analyte ion species are included in a subsequent fragmentation event. However, as the window width becomes narrower, a greater number of product ion analyses 34 are required to obtain complete spectral coverage of an investigated precursor-ion range (e.g., 400-1200 Th, as shown in FIG. 6). This leads to the undesirable situation illustrated in FIG. 2, in which only a few analyses may be dedicated to analysis of an eluting analyte, since a large portion of instrument time will be diverted to other tasks. At the opposite extreme, wide isolation windows require fewer MS-2 analyses to cover the full precursor-ion range but give poor selectivity, possibly leading to false trigger events.

Figure 8A:
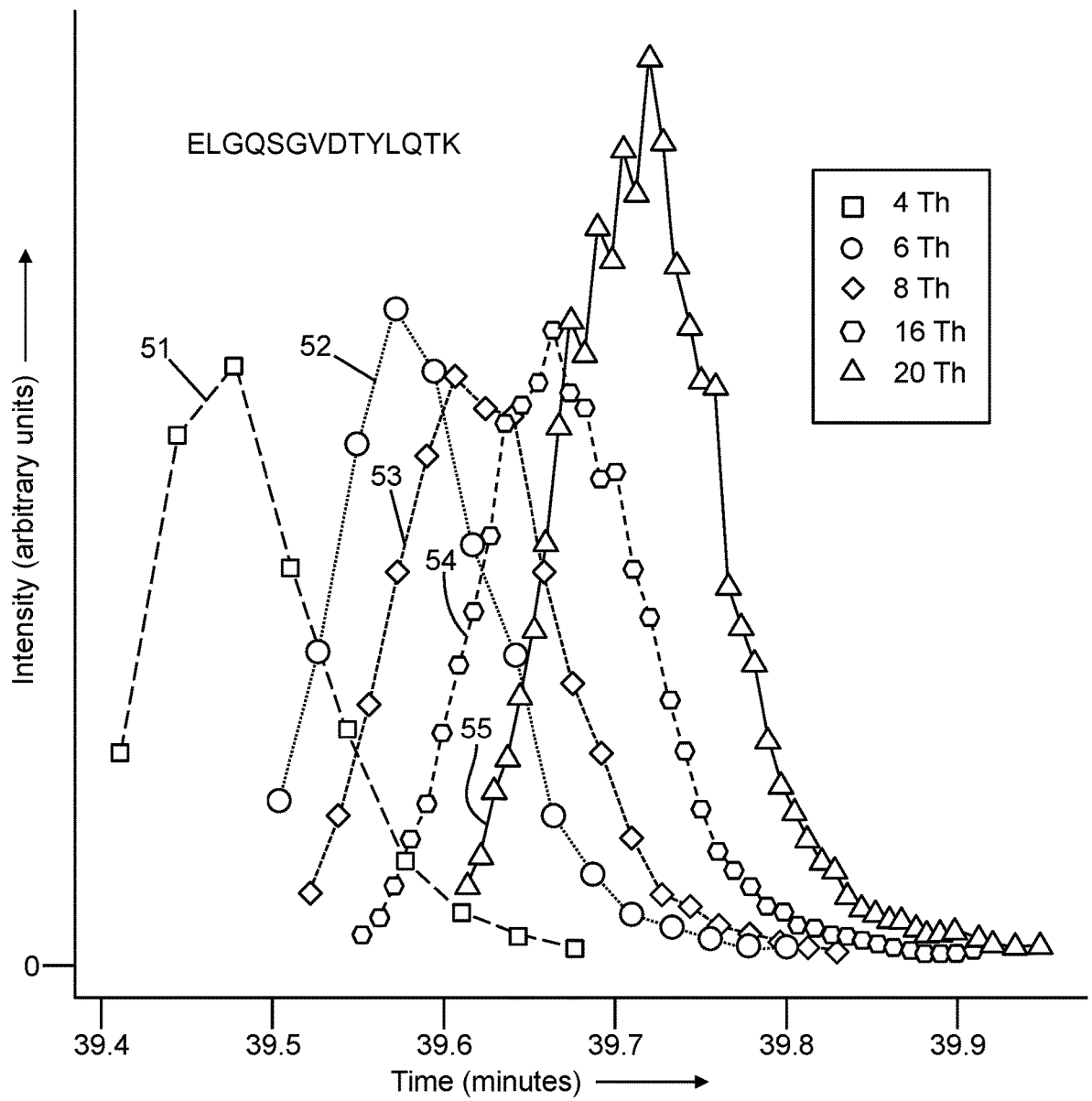
FIG. 8A is a set of graphical plots of the mass spectrometer signal, as generated in accordance with the present teachings and using various mass isolation widths, of a labeled version of the peptide ELGQSGVDTYLQTK.
Figure 8B:
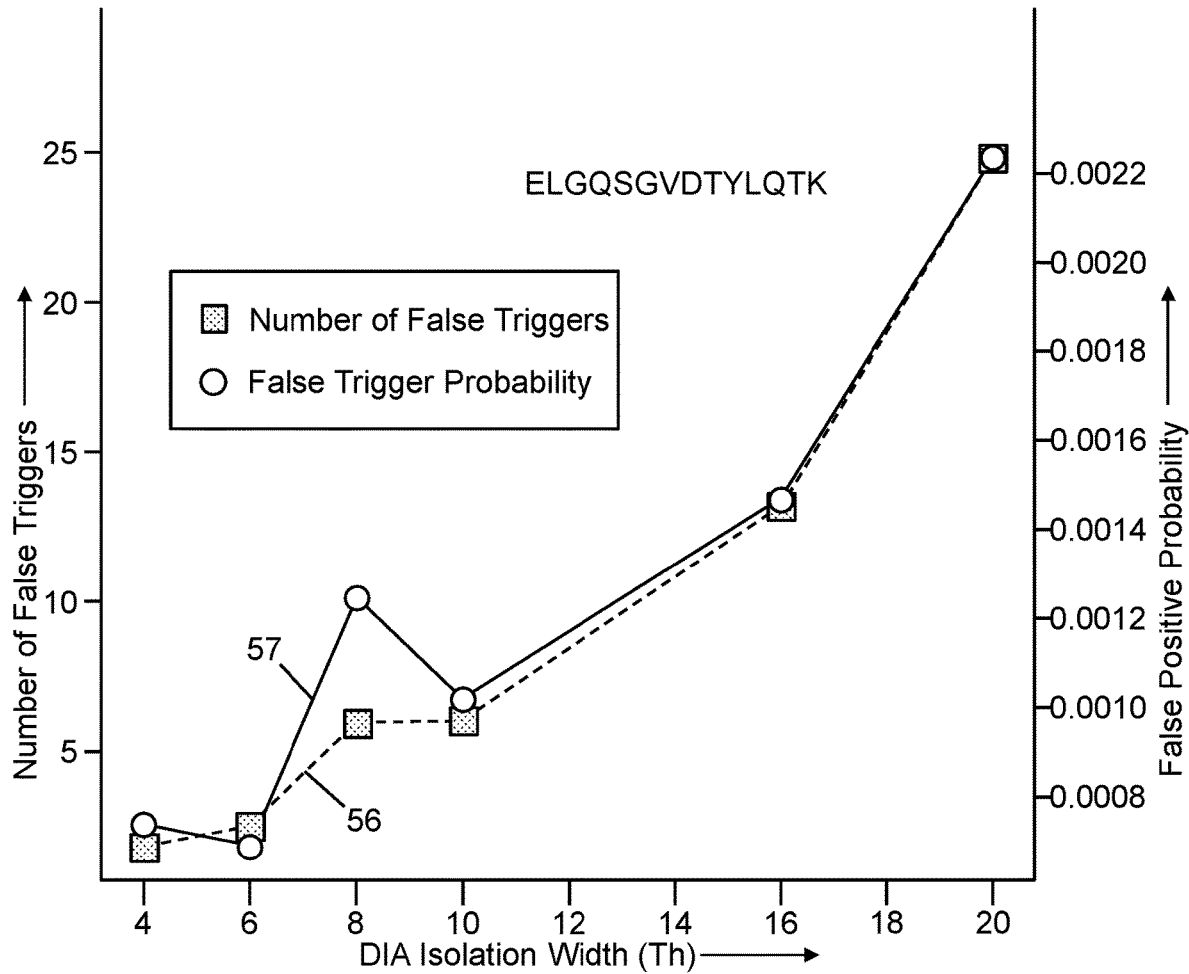
FIG. 8B is a graph showing plots of the total number of observed false quantitative-analysis triggers and the percentage of such observed triggers versus mass isolation width, as observed during mass analysis of a labeled version of the peptide ELGQSGVDTYLQTK in accordance with the present teachings.

The inventors have conducted experiments to assess the degree of false triggering that may be expected when performing methods in accordance with the present teachings using an ion trap mass analyzer. FIGS. 8A-8B relate to the effects of isolation window width on the rate of false triggering and the degree of chromatographic peak coverage. The plots in FIGS. 8A-8B relate to analysis of the peptide ELGQSGVDTYLQTK, which is a component of the PRTC mixture. The peptide ELGQSGVDTYLQTK was analyzed in parallel together with the fourteen other peptide components of the PRTC over the course of the analyses that produced the data illustrated in FIGS. 8A-8B.

The analyses depicted in FIGS. 8A-8B were repeated using different precursor-ion isolation widths as shown in FIG. 8A-8B. Specifically, peak traces 51, 52, 53, 54, and 55 in FIG. 8A relate to experimental runs performed using isolation window widths of 4 Th, 6 Th, 8 Th, 16 Th and 20 Th, respectively. FIG. 8A depicts the integrated mass spectral peak intensity data peptide ELGQSGVDTYLQTK as measured at different retention times. The traces 51-55 are offset from one another, parallel to the abscissa, as a result of retention-time drift over the course of several sample injections as a result of column aging. This is a common issue which may be addressed by methods in accordance with the present teachings as discussed further below. FIG. 8B depicts the total number of observed false triggers (plot 56) and the derived false-trigger probability (plot 57) for the measurement of this peptide.

The data depicted in FIGS. 8A-8B indicate that, under the described experimental conditions and with chromatographic peaks that are approximately eighteen seconds wide, narrow isolation window widths of less than 10 Th generate a negligible number of false triggers but cause a significant under-sampling of the peaks. Conversely, peak isolation widths of 20 Th generate good spectral coverage across each chromatographic peak but increase the probability of observing falsely triggered analyses by a factor of 5-6. Interestingly, however, even with the widest isolation windows investigated, the number of false triggers is better than is generally observed during parallel targeted analyses obtained using conventional methods.

Figure 4:
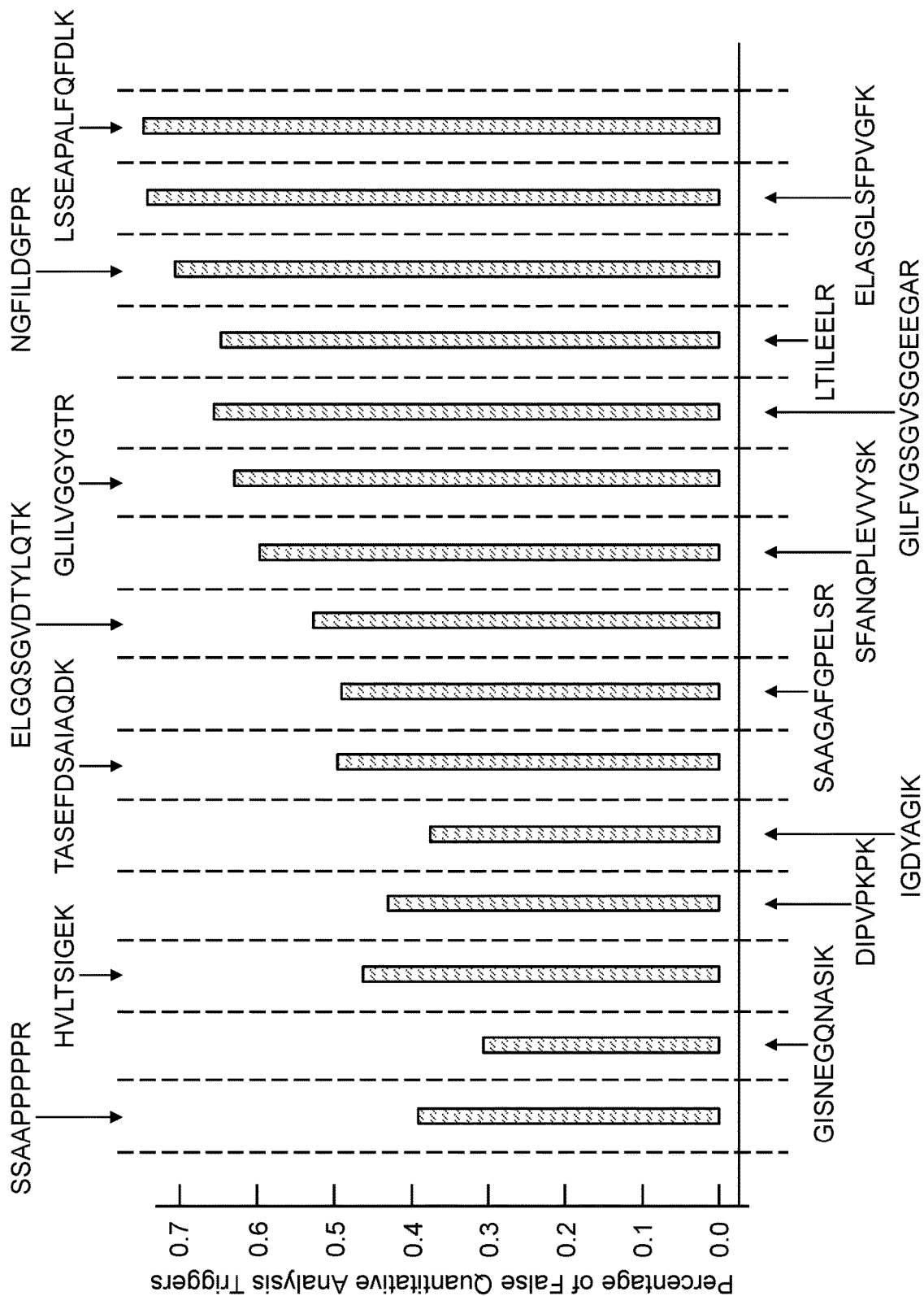
FIG. 4 is a bar chart showing the percentage of false quantitative analysis triggers that are obtained when conducting parallel targeted quantitative analyses, using a quadrupole ion trap mass analyzer and in accordance with the known SureQuant™ method, of the peptides: SSAAPPPPPR; GISNEGQNASIK; HVLTSIGEK; DIPVPKPK; IGDYAGIK; TASEFDSAIAQDK; SAAGAFGPELSR; ELGQSGVDTYLQTK; SFANQPLEVVYSK; GLILVGGYGTR; GILFVGSGVSG-GEEGAR; LTILEELR; NGFILDGFPR; ELASGLSFPVGFK; and LSSEAPALFQFDLK.
Figure 9:
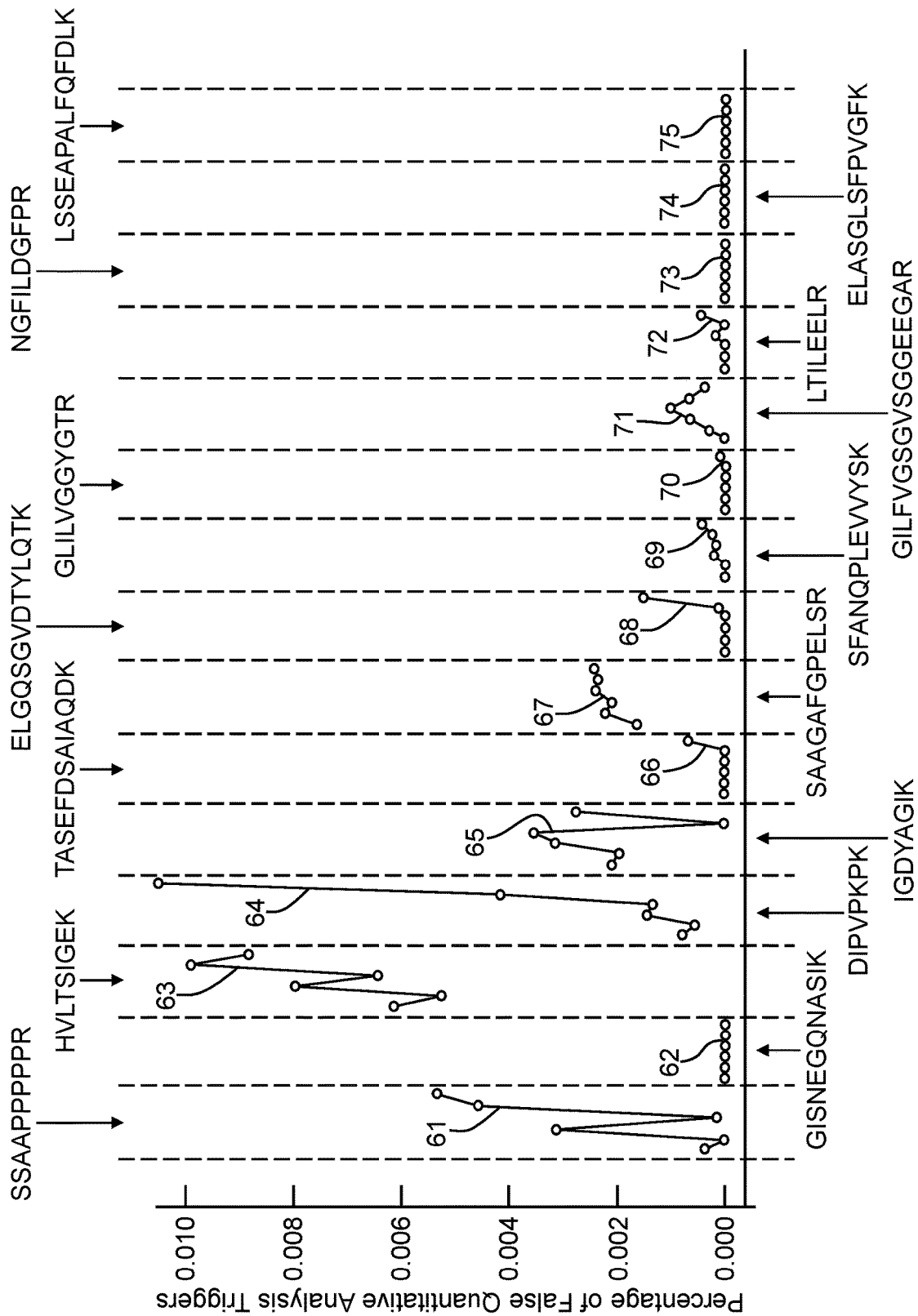
FIG. 9 is a set of plots showing the percentage of false quantitative analysis triggers that are obtained when conducting parallel targeted quantitative analyses, using a quadrupole ion trap mass analyzer and in accordance with the present teachings, of the labeled peptides: SSAAPPPPPR; GISNEGQNASIK; HVLTSIGEK; DIPVPKPK; IGDYAGIK; TASEFDSAIAQDK; SAAGAFGPELSR; ELGQSGVDTYLQTK; SFANQPLEVVYSK; GLILVGGYGTR; GILFVGSGVSGGEEGAR; LTILEELR; NGFILDGFPR; ELASGLSFPVGFK; and LSSEAPALFQFDLK.

FIG. 9 is a set of plots showing the percentage of false quantitative analysis triggers that are obtained when conducting parallel targeted quantitative analyses using a quadrupole ion trap mass analyzer and in accordance with the present teachings, of the labeled peptides: SSAAPPPPPR (plot 61); GISNEGQNASIK (plot 62); HVLTSIGEK (plot 63); DIPVPKPK (plot 64); IGDYAGIK (plot 65); TASEFDSAIAQDK (plot 66); SAAGAFGPELSR (plot 67); ELGQSGVDTYLQTK (plot 68); SFANQPLEVVYSK (plot 69); GLILVGGYGTR (plot 70); GILFVGSGVSGGEEGAR (plot 71); LTILEELR (plot 72); NGFILDGFPR (plot 73); ELASGLSFPVGFK (plot 74); and LSSEAPALFQFDLK (plot 75). Specifically, each of traces 61-75 of FIG. 9 is a plot of the probability of the occurrence of false positive quantitative-analysis triggers versus isolation window width, as determined for isolation window widths of 4 Th, 6 Th, 8 Th, 10 Th, 16 Th and 20 Th. (Note that there is a respective implied abscissa (not shown for clarity) between each pair of vertical dashed lines in FIG. 9 that records values of Δ(m/z), in units of thomsons.) Comparison with the data of FIG. 4 shows that adjustment of the Internal-Standard-Triggered methods to better match quadrupole ion trap figures of merit results in far more efficient acquisition than would otherwise result basic transfer of the original methods to such instruments. Accordingly, by practicing the methods of the present teachings, mass spectrometer systems that utilize quadrupole ion trap mass analyzers for parallel reaction monitoring can achieve efficiency benefits similar to those known for Internal-Standard-Triggered methods, without significant loss in the quality of the results.

Figure 10A:
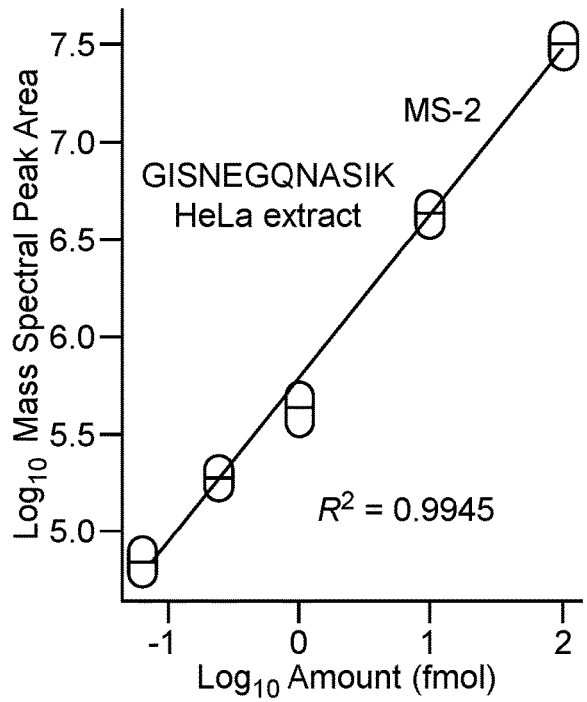
FIG. 10A is a plot of the logarithm of measured mass spectral peak area, versus the logarithm of the known amount of the peptide GISNEGQNASIK within a HeLa extract sample, the mass spectral peak area being generated by MS-2 mass spectrometry in accordance with a method of the present teachings.
Figure 10B:
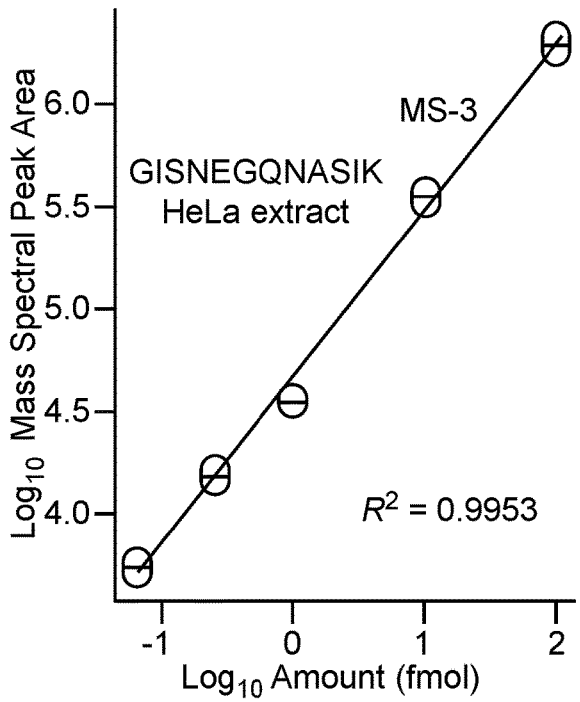
FIG. 10B is a plot of the logarithm of measured mass spectral peak area, versus the logarithm of the known amount of the peptide GISNEGQNASIK within a HeLa extract sample, the mass spectral peak area being generated by MS-3 mass spectrometry in accordance with a method of the present teachings.
Figure 11A:
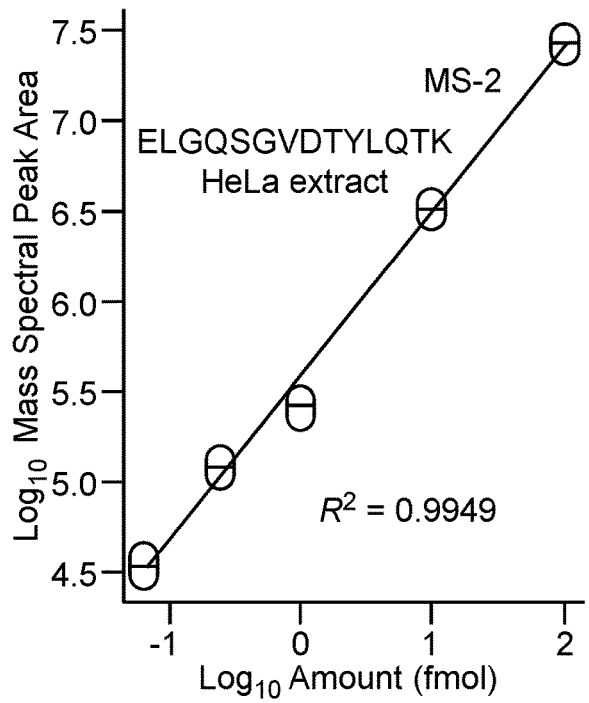
FIG. 11A is a plot of the logarithm of measured mass spectral peak area, versus the logarithm of the known amount of the peptide ELGQSGVDTYLQTK within a HeLa extract sample, the mass spectral peak area being generated by MS-2 mass spectrometry in accordance with a method of the present teachings.
Figure 11B:
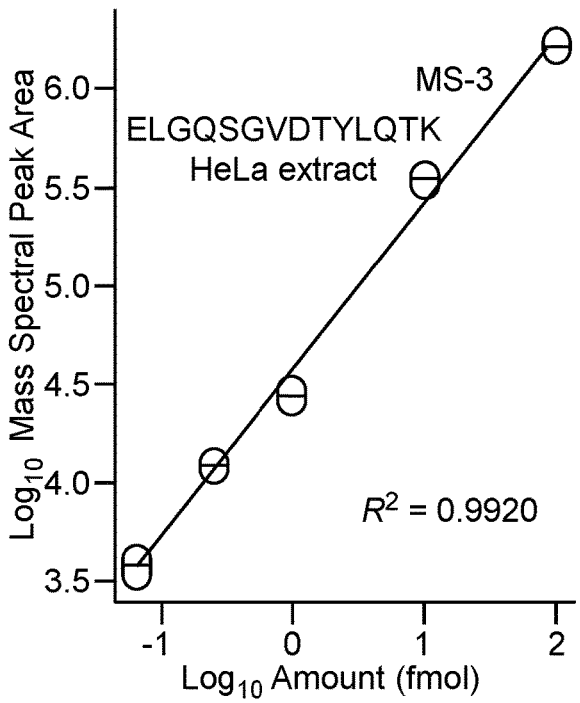
FIG. 11B is a plot of the logarithm of measured mass spectral peak area, versus the logarithm of the known amount of the peptide ELGQSGVDTYLQTK within a HeLa extract sample, the mass spectral peak area being generated by MS-3 mass spectrometry in accordance with a method of the present teachings.

FIGS. 10A-10B are log-log plots of measured mass spectrometer signal versus known concentrations of the peptide GISNEGQNASIK. The data displayed in FIG. 10A-10B as well as in FIGS. 11A-11B and 12-15 were obtained on labeled peptides included in the Pierce 7×5 System Suitability Test kit, available from Thermo Fisher Scientific of Waltham, Massachusetts USA, after spiking the mixture of standard peptides into a HeLa extract sample at a concentration of 0.4 µg/µL. The Pierce 7×5 System Suitability Test mixture comprises five differently labeled isotopologues of each one of seven peptides. The different isotopologues of each peptide are present in the mixture at different concentrations, which range from 100 fmol/µL to 0.065 fmol/µL. The results shown in FIG. 10A relate to MS-2 quantitative analyses whereas the results shown in FIG. 10B relate to MS-3 quantitative analyses. FIGS. 11A-11B show similar results for the peptide ELGQSGVDTYLQTK. These data were obtained by mass analysis of the labeled peptides of the Pierce 7×5 System Suitability Test kit, as spiked into a HeLa extract sample, as described above. The five data points shown in each plot relate to the five different isotopologues of each peptide that are constituents of the test kit. The results depicted in each plot were generated in accordance with the present teachings and using the most abundant labeled isotopologue of each peptide as the "internal standard" for purposes of triggering analyses of the other isotopologues. The straight lines shown in each plot are linear best-fits to the data; the $R^2$ values relate to the goodness of the fits.

Figure 12:
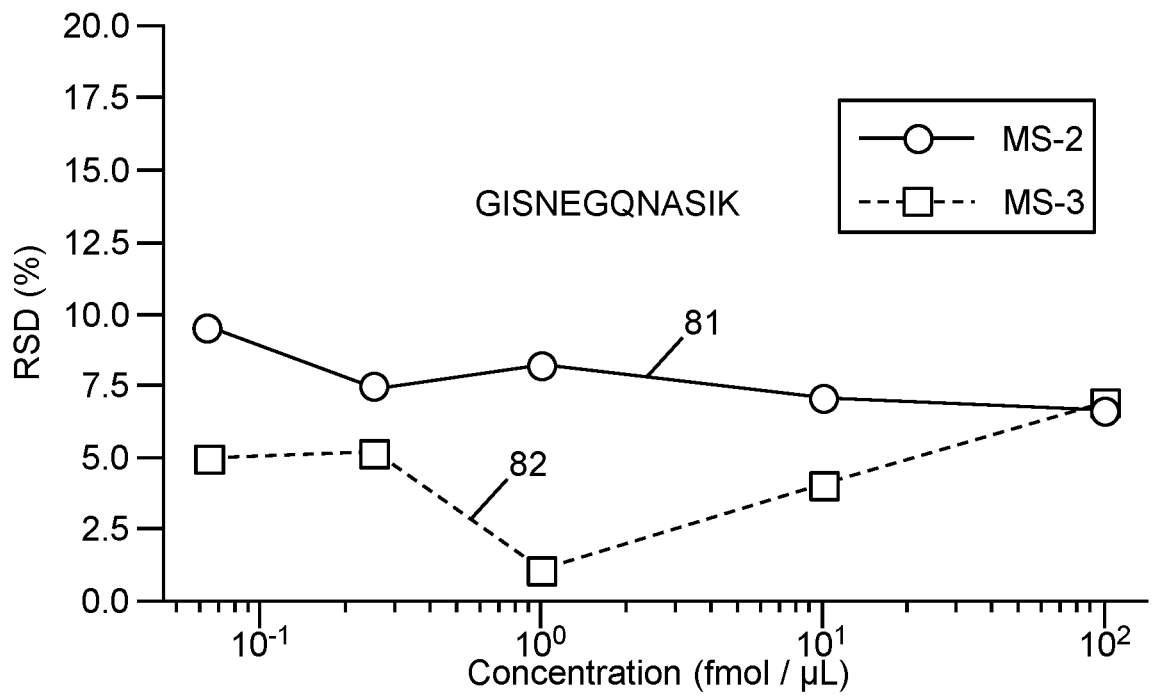
FIG. 12 is a plot of relative standard deviation (RSD), plotted as a percentage, of the mass spectrometer signal of the peptide GISNEGQNASIK versus the concentration (in fmol per µL, plotted on a logarithmic scale) of that peptide, the relative standard deviation determined from replicate quantitative MS-2 mass spectrometer measurements and replicate MS-3 mass spectrometer measurements obtained in accordance with a method of the present teachings.
Figure 13:
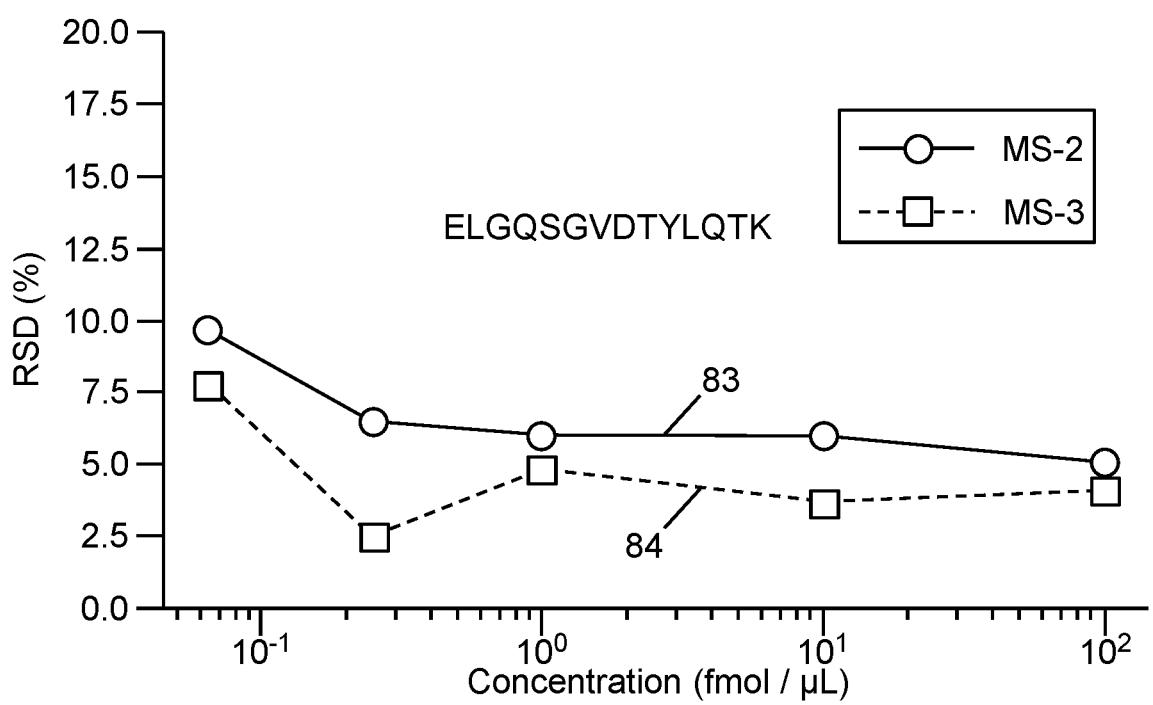
FIG. 13 is a plot of relative standard deviation (RSD), plotted as a percentage, of the mass spectrometer signal of the peptide ELGQSGVDTYLQTK versus the concentration (in fmol per µL, plotted on a logarithmic scale) of that peptide, the relative standard deviation determined from replicate quantitative MS-2 mass spectrometer measurements and replicate MS-3 mass spectrometer measurements obtained in accordance with a method of the present teachings.
Figure 14:
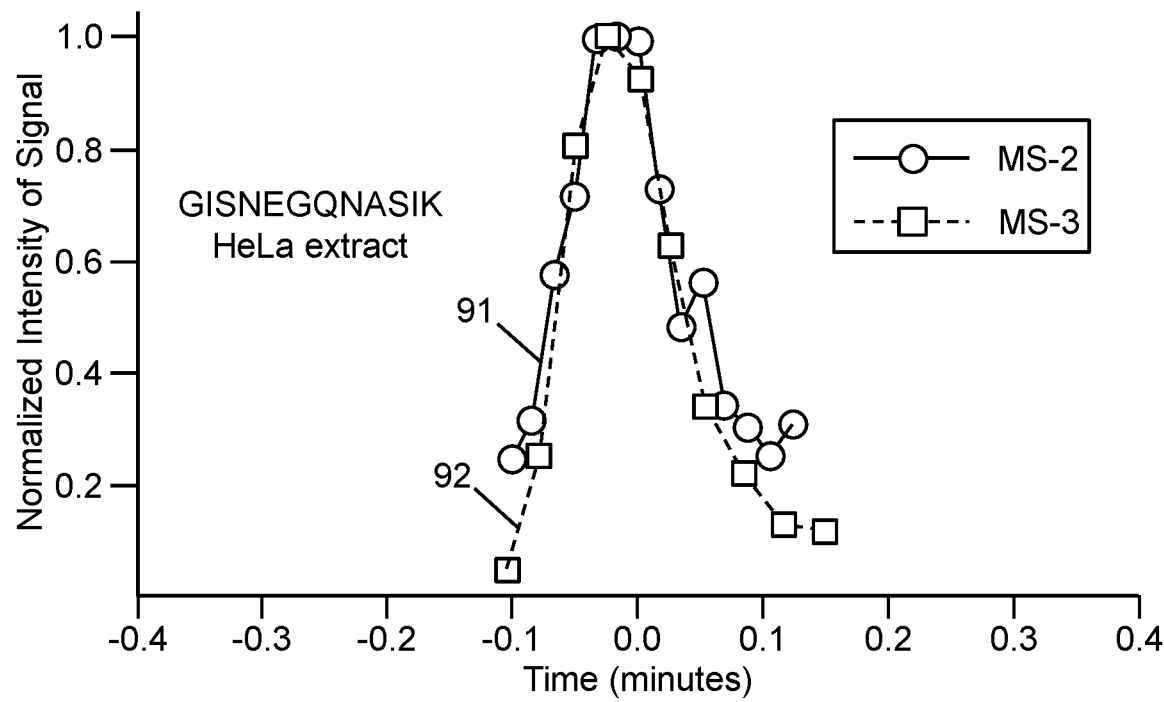
FIG. 14 is a plot, versus time, of the normalized intensity of mass spectrometer signals, as generated in accordance with a method of the present teachings and employing MS-2 and MS-3 mass spectra, of 65 amol of the peptide GISNEGQNASIK within a HeLa extract sample.
Figure 15:
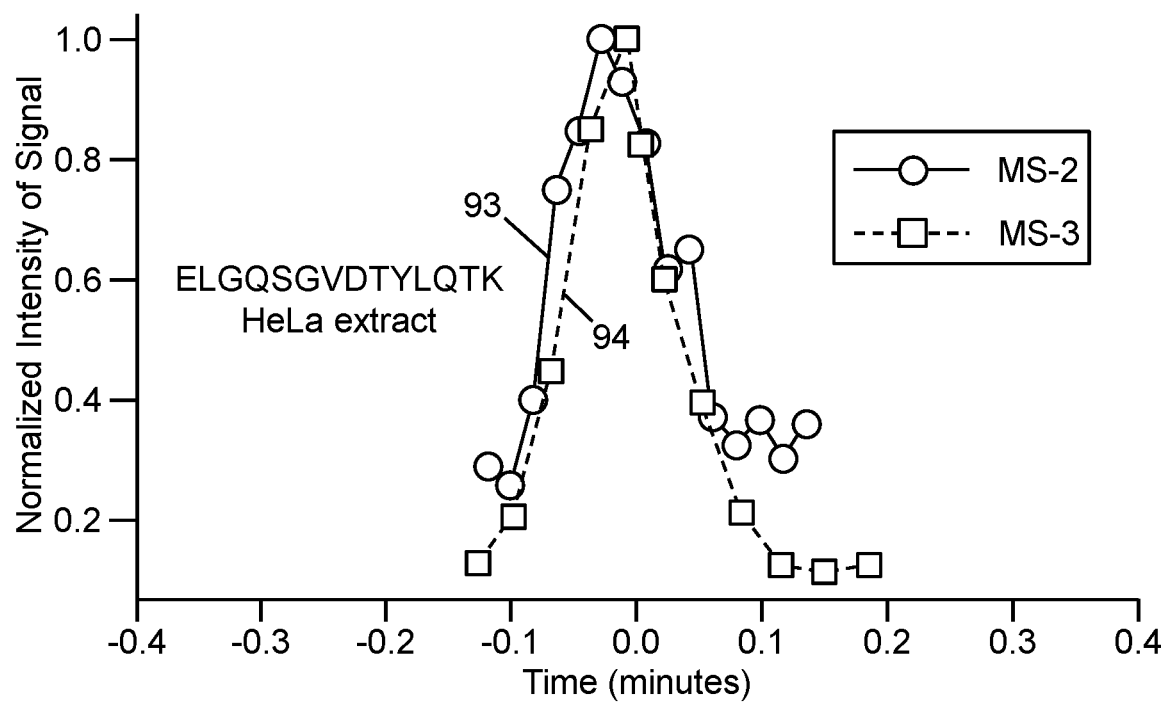
FIG. 15 is a plot, versus time, of the normalized intensity of mass spectrometer signals, as generated in accordance with a method of the present teachings and employing MS-2 and MS-3 mass spectra, of 65 amol of the peptide ELGQSGVDTYLQTK within a HeLa extract sample.

FIGS. 12 and 13 are plots of relative standard deviation versus concentration for the two peptides GISNEGQNASIK and ELGQSGVDTYLQTK. The plots in FIGS. 12 and 13 relate to the same data that was used to generate the plots of FIGS. 10A-10B and FIGS. 11A-11B. Traces 81 and 83 relate to MS-2 data; traces 82 and 84 relate to MS-3 data. The relative standard deviations (RSDs) of the mass spectrometer signal that are indicated in FIG. 13 are based upon five replicate analyses, which were not normalized to the signal of the most abundant isotopologue. These data indicate that MS-3 analyses produce results that are somewhat more precise than the MS-2 analyses. These conclusions are supported by the actual elution peaks of the two peptides obtained at the lowest concentration (65 amol) as shown in FIGS. 14-15. In these latter two plots, traces 91 and 93 relate to MS-2 data whereas traces 92 and 94 relate to MS-3 data. The data depicted in FIGS. 14-15 exhibit a lower baseline for the MS-3 analyses relative to the MS-2 analyses, reflecting the better signal-to-noise ratio for the MS-3 analyses. These features are presumably the result of the better exclusion of ion species of non-analyte compounds that is offered by MS-3 analysis.

Figure 16A:
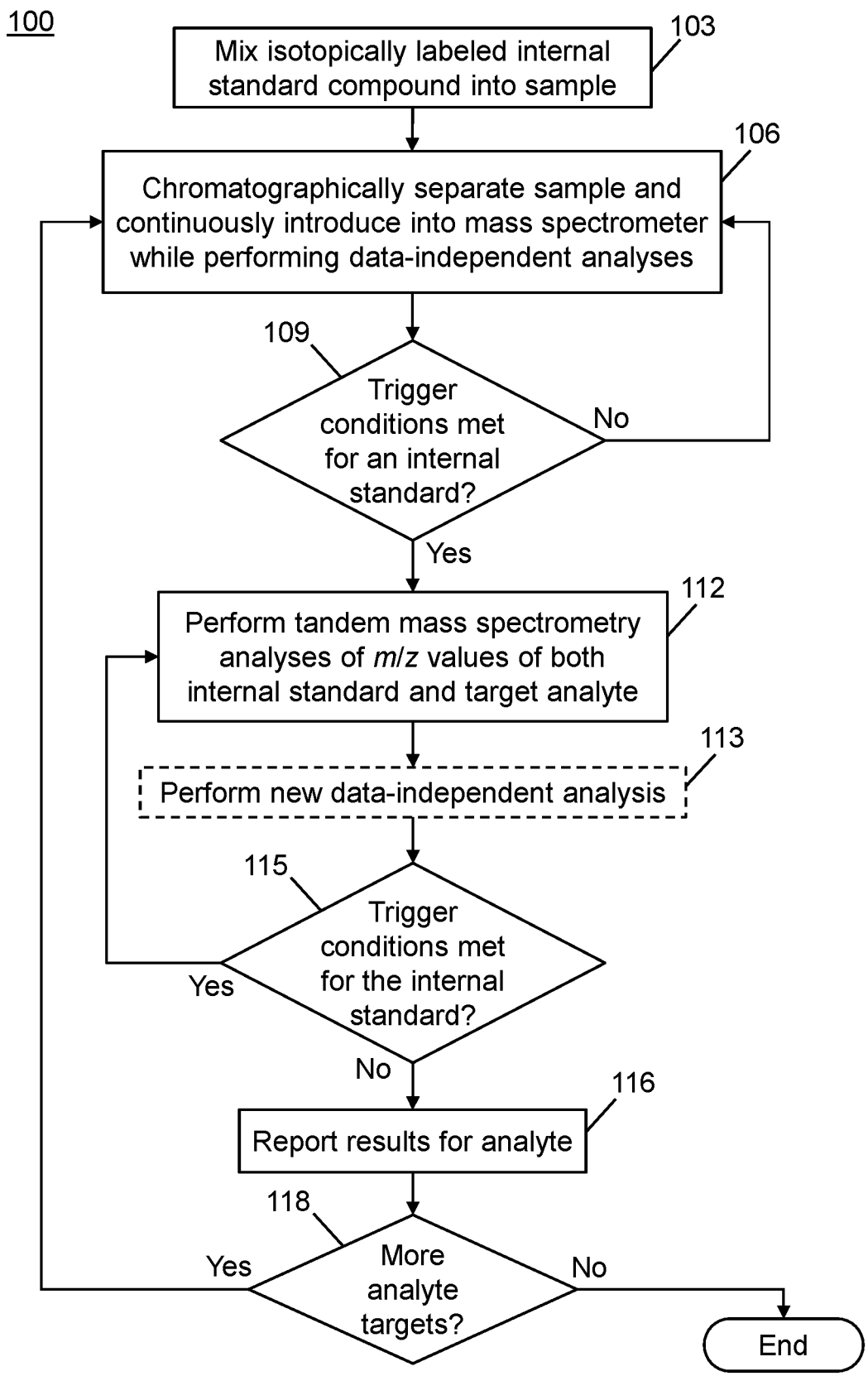
FIG. 16A is a flow diagram of a method for performing a targeted quantitative LCMS analysis of a peptide in accordance with the present teachings.

FIG. 16A is a flow diagram of a first automated method for performing a targeted quantitative LCMS analysis of a peptide analyte within a sample in accordance with the present teachings. As shown in FIG. 16A, the first step, step 103, of the method 100 is to add an internal standard compound into the sample at a known concentration, the internal standard compound comprising an isotopically labeled version of the targeted analyte. In step 106, the sample containing the internal sample is introduced into a liquid chromatograph (LC) apparatus (e.g., LC apparatus 11 as depicted in FIG. 1) of the LCMS system at the same time the related mass spectrometer apparatus (MS) performs repeated data independent analyses. Within this step, the liquid chromatograph separates the various chemical constituents of the sample in known fashion and, as the separation occurs, the eluate is introduced into the mass spectrometer component (e.g., mass spectrometer 13). Because the exogenous internal standard is chemically similar to the endogenous targeted analyte, both the internal standard and analyte (if present) elute simultaneously, essentially within a single chromatographic separate. That same separate may also include molecules of other unrelated compounds that elute at the same time.

Each eluting separate is introduced into the mass spectrometer at a time corresponding to its respective retention time. As molecules of each chemical separate are received by the mass spectrometer, they are ionized by ion source 14. The resulting ions comprise a range of m/z values, such as the range 400-1200 Th indicated in FIG. 6. A mass filter 17 sequentially filters the ion species within the full range of m/z values into a plurality of subsets of ion species, each subset comprising ion species having a smaller m/z range, herein referred to as an m/z "window". Example window m/z ranges are indicated by the positions and heights of the shaded rectangles 34 shown in FIG. 6. The process of filtering ions so as to yield a subset of ions comprising a smaller m/z window is often referred to as "selection" of ion species. Because the time required to perform the above-described mass spectrometer operations (i.e., ionization, filtering, selection) is much less than the width, in time, of elution peaks corresponding to the various eluting separates, each m/z window of each cycle that is shown in FIG. 6 may be considered to comprise a subset of ion species from just a single separate.

The ions of the various m/z windows are transferred to a fragmentation or reaction cell 18 that is operable to fragment the ions, thereby generating a plurality of product ions comprising a plurality of product ion species. The product ions resulting from fragmentation of selected ion species within each m/z window are mass analyzed by a mass analyzer 15 and its associated detector 16. The detector generates a signal that corresponds to the product ions that result from fragmentation of selected ion species within each m/z window. The signal corresponding to each window may be referred to as an MS-2 spectrum. This MS-2 spectrum may be recorded in computer-readable electronic data storage 23 for subsequent digital analysis by the programmable processor 19. Each MS-2 spectrum comprises a respective observed intensity (e.g., as represented by a peak-area score) for each m/z value, where each intensity corresponds to the number of ions observed at the corresponding m/z value. Each series of MS-2 analyses, such as the series 35a and 35b indicated in FIG. 6, may be referred to as a single data independent analysis (DIA or, loosely, "DIA analysis"). Optionally, one or more of the DIA analyses may include a full-scan MS-1 survey mass spectrum 32 which is a record of all of the various ions, comprising multiple ion species, as generated by an ion source in the absence of controlled fragmentation.

In step 109 of the method 100 (FIG. 16A), one or more MS-2 spectra of a DIA analysis are examined in order to determine if a set of MS-2 mass spectral lines satisfy degree-of-matching conditions that are determined from one or more degree-of-matching scores, where the scores are measures of either mass spectral intensity or peak area or of overall similarity between observed mass spectral lines and the mass spectral lines that are expected for the internal standard. If an MS-1 survey mass spectrum 32 has been acquired, then the calculation of the degree-of-matching scores may include one or more lines from that spectrum as well. The internal standard data, including the positions and relative intensities of the internal standard's MS-2 lines, may be entered by a user prior to the beginning or targeted analyses or else may be tabulated in a database that is stored on electronic data storage device 23. Preferably, the degree-of-matching scores comprise peak area and spectral contrast scores as described above herein, possibly supplemented by a retention-time matching score based on an observed difference between an observed and an expected retention time. However, any suitably reliable degree-of-matching score calculation scheme may be employed in this step.

If, in step 109, the degree-of-matching conditions are met, then a quantitative mass analysis of the matched internal standard and a quantitative mass analysis of the endogenous peptide that corresponds to the internal standard are executed in step 112. The quantitative analysis of the internal standard may comprise maintaining a record of or a running total of integrated or summed peak areas of peaks attributable to the internal standard. The quantitative analysis of the analyte comprises maintaining a record of or a running total of summed raw mass spectrometer signals at m/z positions where corresponding peaks of the targeted analyte, if present, either occur or are expected to occur. These m/z positions are accurately known based on the known mass difference between the exogenous labeled internal standard and the corresponding endogenous analyte. Preferably, these quantitative analyses are executed with greater sensitivity (e.g., longer signal acquisition times) than the sensitivity at which the DIA analyses are executed. Preferably, these quantitative analyses are also carried out with m/z isolation of selected precursor ions that is narrower than the isolation window widths used for the DIA analyses.

The quantitative analyses are carried out until the trigger conditions are no longer met, as determined in step 115, which may utilize the quantitative spectra of the internal standard as bases for its determinations. Accordingly, step 112 may be repeated a plurality of times. However, in accordance with the present teachings, DIA analyses continue periodically over the entire time period of an experimental run. Thus, at least occasionally, the repetitions of the step 112 will be interrupted by step 113 (shown with a dashed line to indicate that it may not occur over the course of every iteration of the loop comprising steps 112 and 115) in which a new DIA analysis is executed. Over the course of the quantitative analyses, a record, such as a running summation, is made of the signal intensities of selected m/z values corresponding to both the exogenous internal standard and the endogenous analyte. The m/z values of the analyte are determined from known m/z offsets between the "heavy" internal standard ion species and the "light" monoisotopic peptide ion species.

The step 109 may be executed after each cycle of MS-2 data acquisitions, such as the cycles 35a and 35b indicated in FIG. 6. Alternatively, this step may be executed periodically after every N consecutive product-ion analyses 34 where the integer, N, is either predetermined prior to measurements. Depending upon the particular analytes being targeted, it may be the case that, at some retention time values, a plurality of elution peaks of various analytes will overlap in time. In order to detect such multiple co-eluting analytes, the quantitative analyses may be interspersed with continued DIA analyses, as described above. Once the trigger conditions for detecting the elution of a particular analyte are no longer met, after having been met previously (at step 115 of the method 100), then the results of the quantitative analyses of the analyte and corresponding internal standard are reported in step 116. The reporting includes storing either raw data or derived quantities in electronic data storage 23 and may include reporting condensed results to a user by means of a visual display or printed information. Further DIA analyses may resume if, at step 118, there are remaining analyte targets at later retention times or if a scheduled experimental run time has not completed.

Figure 16B:
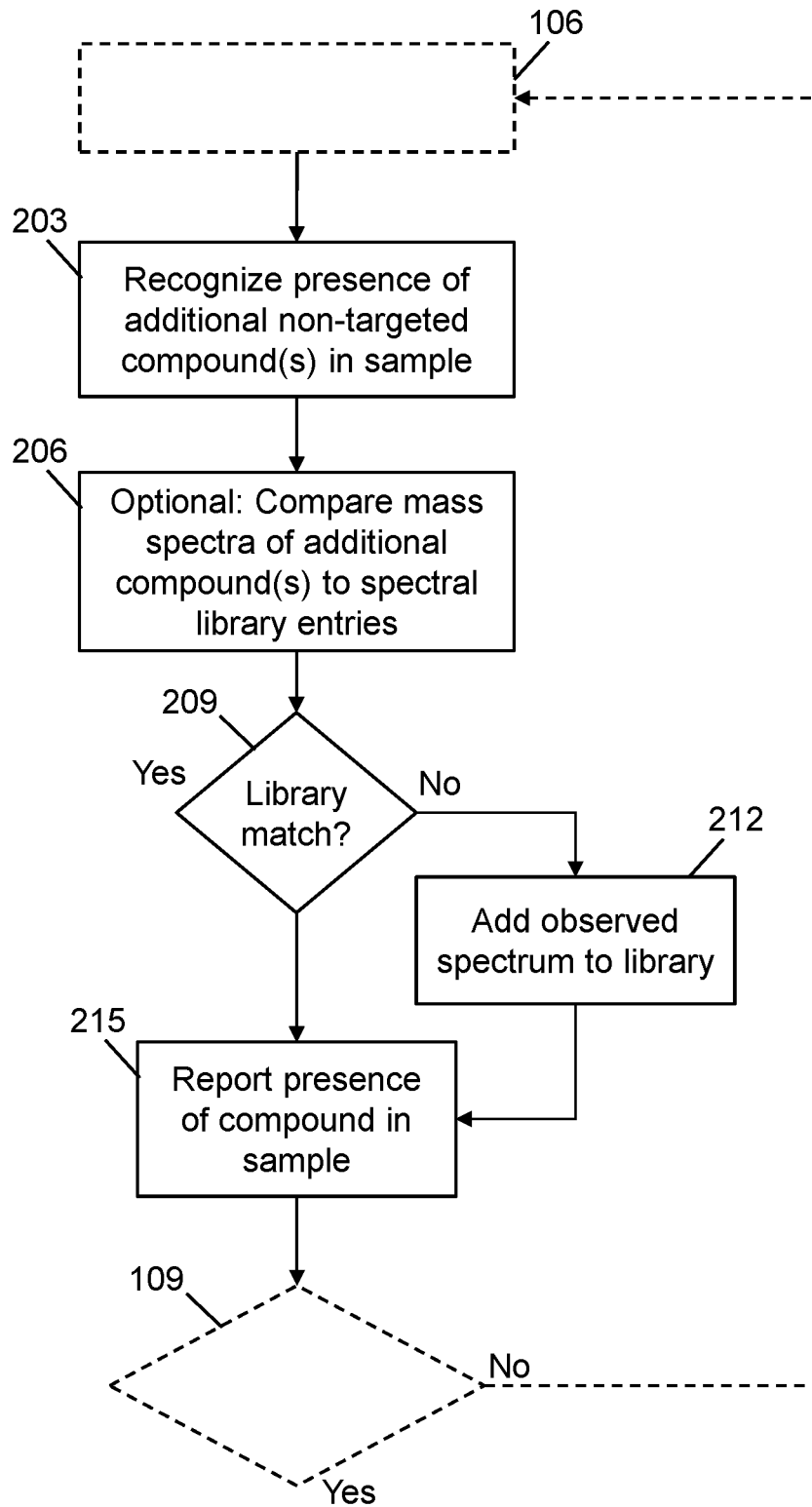
FIG. 16B is a partial flow diagram of another method for performing a targeted quantitative LCMS analysis in accordance with the present teachings.

FIG. 16B is a partial flow diagram of another method for performing a targeted quantitative LCMS analysis in accordance with the present teachings. The method 200 that is diagramed in FIG. 16B includes all of the steps of the method 100 (FIG. 16A) plus some additional steps which are illustrated as steps 203-215 in FIG. 16B. These additional steps improve operational efficiency of an LCMS system by making productive use of the times, during chromatographic separation, when none of the targeted analytes are eluting. The inclusion of these steps is made possible by the fact that, in accordance with the present teachings, information-rich DIA analyses are provided between the elution periods of the targeted analytes. To avoid repetition, the various steps of the method 100, which are included in the method 200, are not depicted in FIG. 16B except for the steps 106 and 109, which are illustrated with dashed lines in order to provide context to the additional steps 203-215.

In accordance with the present teachings and as outlined in the method 200 of FIG. 16B, the plurality of DIA analyses that are performed may be used to survey for the presence of non-targeted-analyte compounds within a sample. For example, the time periods that are not used for quantitative analyses of peptides may be utilized, in step 203, to recognize the presence of various small-molecule compounds in the sample such as metabolites. The elution of such compounds may be recognized by the occurrence of strong peaks at particular retention-time ranges. The DIA analyses automatically capture the mass spectra of the primary ions and fragment ions of the eluting compounds which are reported, in step 215, including recording raw data and/or derived quantities in electronic data storage 23. In optional step 206, a programmable electronic processor 19 may execute computer instructions that compare, in real time (i.e., simultaneously with continued data acquisition), the experimentally observed mass spectral lines to annotated entries in a library of known spectra. To speed the comparison, the library entries or the library search may be restricted to a particular class of compounds. If a match to a known compound (or possible matches to one of several compounds) is/are likely, then the potential presence of the compound or compounds may be reported, such as by being noted in an experimental record, together with a confidence level. If the observed mass spectral lines do not match any library entry (step 209), then a new non-annotated library entry may be created to record the spectrum of the unidentified compound (step 212). Optionally, when the observed mass spectral lines do not match any library entry, this step 212 may comprise triggering one or more new tandem mass analyses having higher selectivity (i.e., a smaller m/z isolation width) than the preceding DIA analysis in order to more accurately and more unambiguously characterize the mass spectrum of the unidentified compound. The data from the new mass analysis or analyses may be stored in addition to or instead of data acquired from the DIA analysis.

Improved methods and apparatus for targeted mass spectral proteomics analyses have been disclosed herein. The discussion included in this application is intended to serve as a basic description. The present invention is not intended to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. For example, although the teachings herein have been described in terms peptide analyses, the methods described herein would also work for mass analyses of other classes of compounds using heavy labeled analogs of those compounds as internal standards. Such modifications are intended to fall within the scope of the appended claims. While it is believed to be preferable to trigger quantitative mass analyses for both the exogenous and endogenous species (e.g., analyses 25 and 26, respectively, in FIGS. 5A-5B) it may be possible, in certain instances, to only trigger the endogenous quantitative scans, and use data from a time-proximate DIA analysis to determine the amount of the exogenous analyte. Alternatively or additionally, the mass spectrometric signal of the exogenous internal standard from the DIA analyses may be used to normalize across various data acquisition runs in order to make quantitative comparisons between samples of between experiments.

Any patents, patent applications, patent application publications or other literature mentioned herein are hereby incorporated by reference herein in their respective entirety as if fully set forth herein, except that, in the event of any conflict between the incorporated reference and the present specification, the language of the present specification will control.

What is claimed is:

1. A Liquid Chromatography Mass Spectrometry (LCMS) system comprising:
   a chromatograph configured to receive a continuous stream of a sample;
   a mass spectrometer configured to receive separated fractions of the sample from the chromatograph and to ionize said separated fractions, whereby the ionization generates a plurality of precursor ion species; and
   a programmable processor comprising computer-readable instructions that are operable to:
     repeatedly:
       cause the mass spectrometer to perform a data-independent analysis of a subset of the precursor ion species using a mass analyzer of the mass spectrometer, whereby mass spectra of a plurality of product-ion species generated by fragmentation of the precursor ion species are acquired;

calculate one or more degree-of-matching scores that relate to either a number of ions of an internal standard that are detected or to overlap between results of the data-independent analysis and tabulated mass spectral data of the internal standard; and if each of the degree-of-matching scores meets a respective degree-of-matching condition, perform a quantitative tandem mass spectrometric analysis of the internal standard and a quantitative tandem mass spectrometric analysis of the analyte; and calculate a quantity of the analyte in the sample by comparison between intensities of one or more mass spectral signals generated by the quantitative tandem mass spectrometric analyses of the analyte to intensities of one or more mass spectral signals generated by the quantitative tandem mass spectrometric analyses of the internal standard.

2. A system as recited in claim 1, wherein the computer-readable instructions that are operable to cause the mass spectrometer to perform the data-independent analysis of the precursor ion species using the mass analyzer are further operable to cause the mass spectrometer to:

isolate a plurality of subsets of the precursor ion species, each subset comprising a respective range of m/z values;

separately fragment the ion species of each subset of ion species, whereby each fragmenting generates a subset of the product ion species; and separately mass analyze each subset of the fragment ion species.

3. A system as recited in claim 1, wherein the one or more degree-of-matching scores consist of a mass spectral peak-area score and wherein the degree-of-matching condition is met if an observed mass spectral intensity attributable to the internal standard is greater than a predetermined percentage of an expected peak intensity of the internal standard during its elution, wherein the predetermined percentage is within the range of one-to-five percent, inclusive.

4. A system as recited in claim 1, wherein the degree-of-matching scores comprise a mass spectral peak-area score and a mass spectral contrast angle score.

5. A system as recited in claim 4, wherein the degree-of-matching scores further comprise a retention time matching score.

6. A system as recited in claim 4, wherein the degree of matching condition of the mass spectral peak-area score is met only if an observed mass spectral intensity attributable to the internal standard is greater than a predetermined percentage of an expected peak intensity of the internal standard during its elution.

7. A system as recited in claim 6, wherein the mass spectral intensity degree of matching condition is met only if the observed mass spectral intensity attributable to the internal standard is greater than fifty percent of the expected peak intensity of the internal standard during its elution.

8. A system as recited in claim 6, wherein the mass spectral intensity degree of matching condition is met only if the observed mass spectral intensity attributable to the internal standard is greater than thirty percent of the expected peak intensity of the internal standard during its elution.

9. A system as recited in claim 6, wherein the mass spectral intensity degree of matching condition is met only if the observed mass spectral intensity attributable to the internal standard is greater than seventy-five percent of the expected peak intensity of the internal standard during its elution.

10. A system as recited in claim 1, wherein the analyte is a peptide analyte.

11. A system as recited in claim 1, wherein the computer readable instructions that are operable to cause the mass spectrometer to perform a quantitative tandem mass spectrometric analysis of the internal standard and a quantitative tandem mass spectrometric analysis of the analyte are further operable to:

while each of the one or more degree-of-matching scores meets a respective degree-of-matching condition, cause the mass spectrometer to perform a data-independent analysis between the performing of a quantitative tandem mass spectrometric analysis of the internal standard and a performing of a quantitative tandem mass spectrometric analysis of the analyte.

12. A system as recited in claim 1, wherein the computer-readable instructions are further operable to:

recognize, from a data-independent analysis, the presence of an additional non-targeted compound in the sample; and report the presence of the additional non-targeted compound in the sample.

13. A system as recited in claim 12, wherein the non-targeted compound is a non-targeted peptide.

14. A system as recited in claim 12, wherein the recognizing of the presence of the additional non-targeted compound in the sample comprises recognizing the presence of a metabolite compound in the sample.

15. A system as recited in claim 14 wherein the analyte is a peptide analyte.

16. A system as recited in claim 12, wherein the computer-readable instructions are further operable to:

compare mass spectral data obtained by the data-independent analysis and relating to the additional non-targeted compound to entries in a library of mass spectra; and add a new entry to the mass spectral library if the mass spectral data obtained by the data-independent analysis and relating to the additional non-targeted compound does not match any entry in the library.

17. A system as recited in claim 12, wherein the computer-readable instructions are further operable to:

compare mass spectral data obtained by the data-independent analysis and relating to the additional non-targeted compound to entries in a library of mass spectra; and if the mass spectral data obtained by the data-independent analysis and relating to the additional non-targeted compound matches an entry in the mass spectral library, report the presence, within the sample, of the compound that corresponds to the matched spectral library entry.

18. A system as recited in claim 1, wherein the mass analyzer comprises an ion trap mass analyzer.

19. A system as recited in claim 1, wherein the computer readable instructions that are operable to cause the mass spectrometer to perform a quantitative tandem mass spectrometric analysis of the internal standard and a quantitative tandem mass spectrometric analysis of the analyte are further operable to substitute a quantitative MS-3 mass spectrometric analysis for one or both of said quantitative tandem mass analyses.

20. A system as recited in claim 1, wherein the computer readable instructions that are operable to cause the mass spectrometer to perform a quantitative tandem mass spectrometric analysis of the internal standard and a quantitative tandem mass spectrometric analysis of the analyte are operable to cause the mass spectrometer to:
co-isolate ions of the internal standard and ions of the analyte; and
simultaneously fragment the co-isolated ions of the internal standard and the analyte.

21. A Liquid Chromatography Mass Spectrometry (LCMS) system comprising:
a chromatograph configured to receive a continuous stream of a sample;
a mass spectrometer configured to receive separated fractions of the sample from the chromatograph and to ionize said separated fractions, whereby the ionization generates a plurality of precursor ion species; and
a programmable processor comprising computer-readable instructions that are operable to:
repeatedly:
cause the mass spectrometer to perform a data-independent analysis of a subset of the precursor ion species using a mass analyzer of the mass spectrometer, whereby mass spectra of a plurality of product-ion species generated by fragmentation of the precursor ion species are acquired; and
calculate a rate of change of a mass spectrometric signal that relates to a rate of change of a detected number of ions of an internal standard; and
if a magnitude of the calculated rate of change is less than a threshold value, cause the mass spectrometer to:
perform a quantitative tandem mass spectrometric analysis of the internal standard and a quantitative tandem mass spectrometric analysis of the analyte; and
calculate a quantity of the analyte in the sample by comparison between an intensity of a mass spectral signal generated by the quantitative tandem mass spectrometric analyses of the analyte and an intensity of a mass spectral signals generated by the quantitative tandem mass spectrometric analyses of the internal standard.

* * * * *